US011123046B1

(12) United States Patent
Zohar et al.

(10) Patent No.: US 11,123,046 B1
(45) Date of Patent: Sep. 21, 2021

(54) MONITORING THERMAL ABLATION USING REGISTRATION OF B-MODE ULTRASOUND IMAGES

(71) Applicant: TECHSOMED MEDICAL TECHNOLOGIES LTD, Rehovot (IL)

(72) Inventors: Yogev Zohar, Rehovot (IL); Yoshiyasu Shimizu, Kyoto (JP); Gal Peretz, Rehovot (IL); Yossi Abu, Rehovot (IL)

(73) Assignee: TECHSOMED MEDICAL TECHNOLOGIES LTD., Rehovot (IL)

( * ) Notice: Subject to any disclaimer, the term of this patent is extended or adjusted under 35 U.S.C. 154(b) by 0 days.

(21) Appl. No.: 17/088,705

(22) Filed: Nov. 4, 2020

Related U.S. Application Data

(60) Provisional application No. 63/020,079, filed on May 5, 2020.

(51) Int. Cl.
*A61B 8/08* (2006.01)
*A61B 8/00* (2006.01)
*A61B 90/00* (2016.01)

(52) U.S. Cl.
CPC .......... *A61B 8/5246* (2013.01); *A61B 8/0891* (2013.01); *A61B 8/461* (2013.01);
(Continued)

(58) Field of Classification Search
None
See application file for complete search history.

(56) References Cited

U.S. PATENT DOCUMENTS 6,014,473 A 1/2000 Hossack et al.
6,556,695 B1 * 4/2003 Packer ............... A61B 5/02007
382/128
(Continued)

FOREIGN PATENT DOCUMENTS

WO WO 2019/228942 12/2019

OTHER PUBLICATIONS

Jan Kybic and Michael Unser; Fast Parametric Elastic Image Registration; IEEE Transactions on Image Processing, 2003.
(Continued)

*Primary Examiner* — Jonathan Cwern
(74) *Attorney, Agent, or Firm* — Pearl Cohen Zedek Latzer Baratz LLP

(57) ABSTRACT

Systems, displays and methods are provided, for performing ultrasound image registration and for using ultrasound images to guide thermal ablation. Registration is carried out by correlating sequential ultrasound images, identifying key frames from the correlation values, identifying periodic change(s) corresponding to breathing and heart beating, and correlating pixels in sequential key frames that have a same phase with respect to the identifying periodic change(s). Based on the registration, the start of ablation is detected, bubbles formed in the ablation procedure are identified and their movements are followed—all using B-mode ultrasound images only. Using the identified bubbles, the thermally damaged tissue region is demarcated and provided in real-time—at an accuracy similar to prior art post-ablation results. Disclosed systems and methods therefore provide the physician with an ultrasound-based way of monitoring thermal ablation in real-time.

20 Claims, 23 Drawing Sheets
(14 of 23 Drawing Sheet(s) Filed in Color)

(52) U.S. Cl.
CPC .............. *A61B 8/481* (2013.01); *A61B 90/37* (2016.02); *A61B 2090/378* (2016.02)

(56) References Cited

U.S. PATENT DOCUMENTS

| | | | |
|---|---|---|---|
| 7,367,944 B2 | 5/2008 | Rosemberg et al. | |
| 8,603,015 B2* | 12/2013 | Rosemberg | A61B 8/0833 |
| | | | 601/3 |
| 9,675,819 B2* | 6/2017 | Dunbar | A61B 34/25 |
| 2009/0105588 A1 | 4/2009 | Emelianov et al. | |
| 2012/0215104 A1 | 8/2012 | Brannan | |
| 2018/0132927 A1 | 5/2018 | Chen et al. | |
| 2018/0333134 A1* | 11/2018 | Dickie | A61B 8/02 |
| 2019/0261945 A1* | 8/2019 | Funka-Lea | G06T 15/205 |
| 2020/0254285 A1* | 8/2020 | Jang | A61B 8/4494 |

OTHER PUBLICATIONS

Jonghye Woo et al; Non-Rigid Ultrasound Image Registration Based on Intensity and Local Phase Information; 2008 Springer Science + Business Media, LLC.; Manufactured in the United States; Apr. 14, 2008.

Challenge on Liver Ultrasound Tracking; CLUST 2014; Proceedings of the MICCAI 2014 workshop; Held in Conjunction with MICCAI 2014, Cambridge, MA, USA, Sep. 14, 2014.

Partial International Search Report dated Aug. 02, 2021 for corresponding PCT Application PCT/IL2021/050515.

\* cited by examiner

Regaining tracking

Loss of tracking

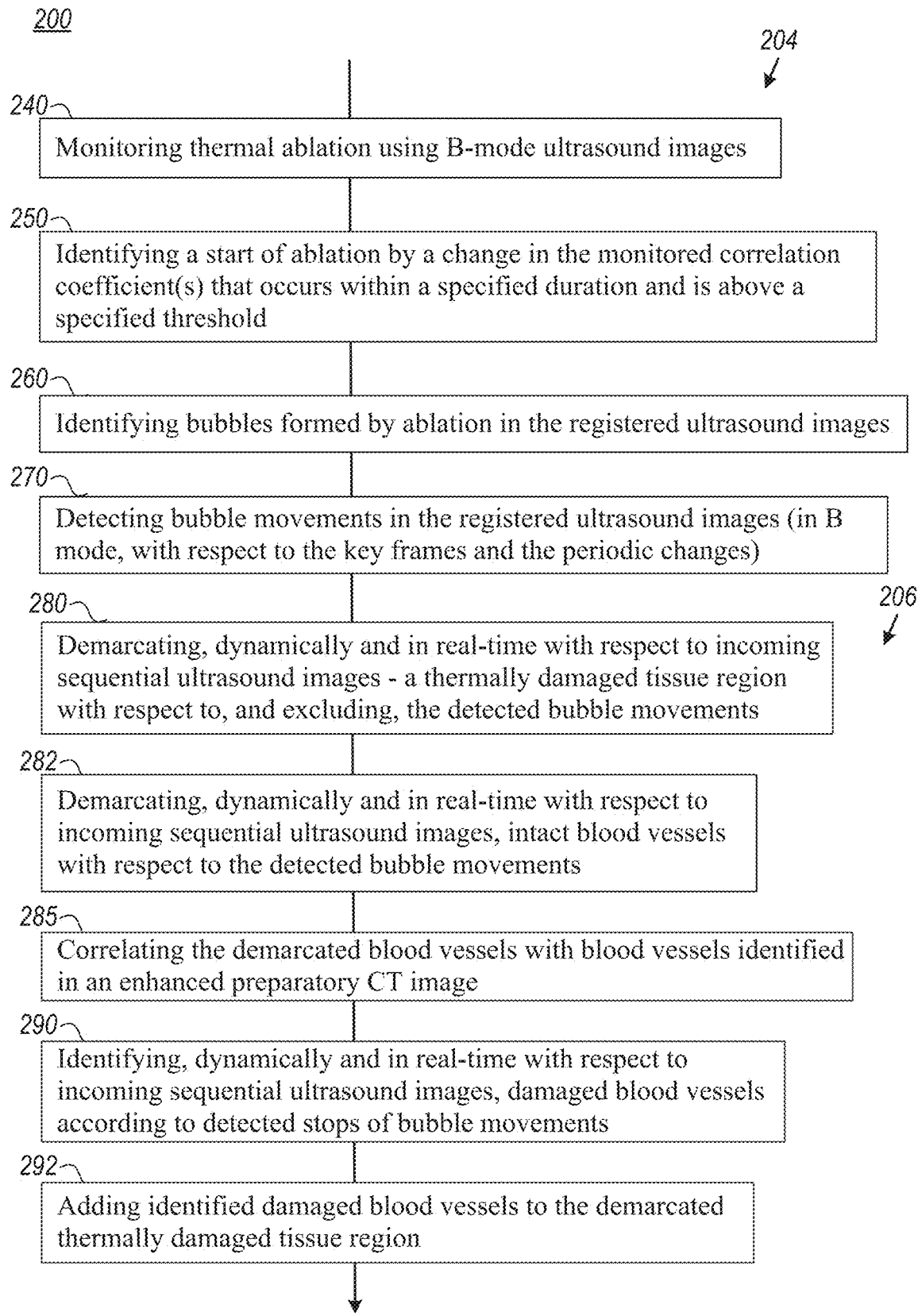
Figure 10 (Continued, 1.)

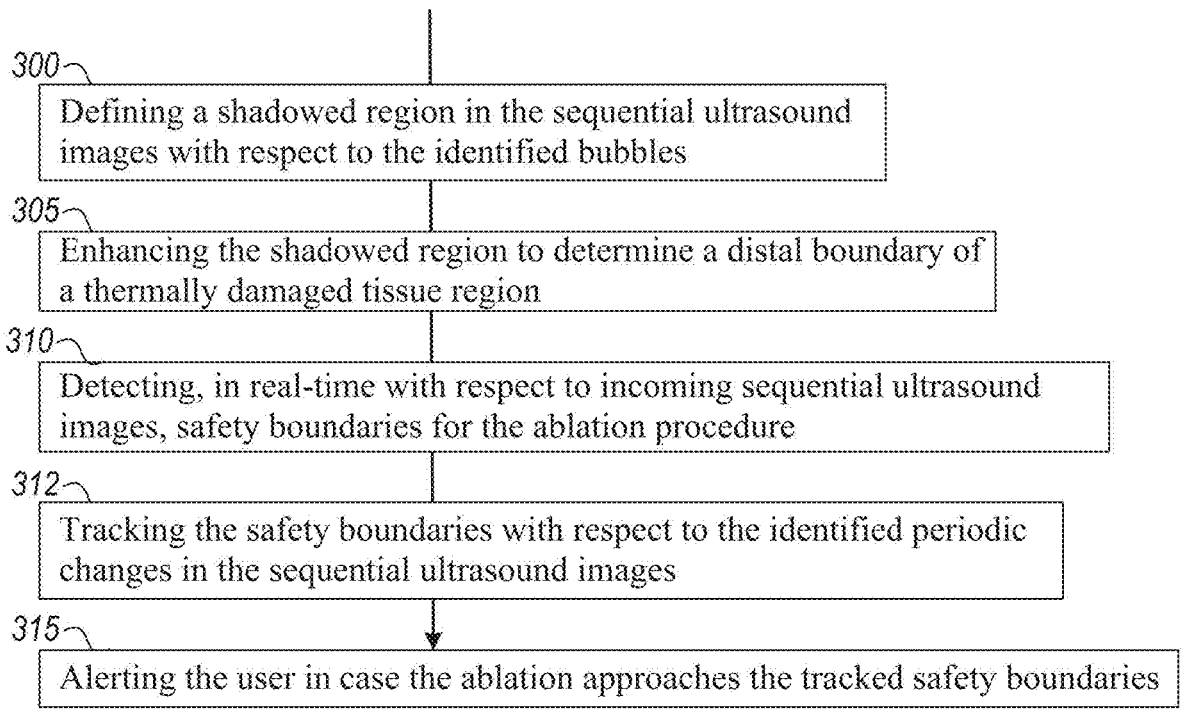
Figure 10 (Continued, 2.)

MONITORING THERMAL ABLATION USING REGISTRATION OF B-MODE ULTRASOUND IMAGES

CROSS REFERENCE TO RELATED APPLICATIONS

This application claims priority from U.S. Provisional Application No. 63/020,079, filed on May 5, 2020, which is incorporated herein by reference in its entirety.

BACKGROUND OF THE INVENTION

1. Technical Field

The present invention relates to the field of thermal ablation, and more particularly, to ultrasound monitoring of thermal ablation procedures.

2. Discussion of Related Art

Current practice uses MRI (magnetic resonance imaging) or CT (computed tomography) to evaluate thermal ablation damage to tissue and ablation procedure efficiency 24 hours after the process takes place and after the tissue has settled. U.S. Pat. Nos. 7,367,944 and 8,603,015 teach methods and systems for monitoring ablation of tissues, and are incorporated herein by reference in their entirety.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides an ultrasound display, associated with a thermal ablation unit, the ultrasound display comprising a repeatedly-updated B-mode ultrasound image, and at least one indication of thermally damaged tissue, registered upon the repeatedly-updated B-mode ultrasound image One aspect of the present invention provides a method of ultrasound image registration that is carried out with respect to a plurality of sequential ultrasound images, the method comprising calculating and correlating the sequential ultrasound images, to yield correlation values, identifying a plurality of key frames from the correlation values, identifying at least one periodic change in the sequential ultrasound images, from the correlation values, and performing the ultrasound image registration by correlating pixels in sequential key frames that have a same phase with respect to the identifying at least one periodic change.

One aspect of the present invention provides a method of monitoring a thermal ablation procedure, comprising identifying a start of ablation by a change in the correlation values that occurs within a specified duration and is above a specified threshold, identifying bubbles formed by ablation in the registered ultrasound images, detecting bubble movements in the registered ultrasound images and demarcating, dynamically and in real-time with respect to incoming sequential ultrasound images, a thermally damaged tissue region with respect to, and excluding, the detected bubble movements.

One aspect of the present invention provides an ultrasound registration module, configured to: calculate and correlate received sequential ultrasound images, to yield correlation values, identify a plurality of key frames from values of the correlation values, identify at least one periodic change in the sequential ultrasound images, from the correlation values, and perform ultrasound image registration by correlating pixels in sequential key frames that have a same phase with respect to the identifying at least one periodic change.

One aspect of the present invention provides an ultrasound image-guided system for thermal ablation, the system comprising: the ultrasound registration module configured to receive a plurality of sequential ultrasound images, and an ablation monitoring module, configured to identify a start of ablation by a change in the correlation values, which occurs within a specified duration and is above a specified threshold.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee."

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 1A-1E are high-level schematic block diagrams of an ultrasound image-guided system for thermal ablation, according to some embodiments of the invention.

Figure 2A:
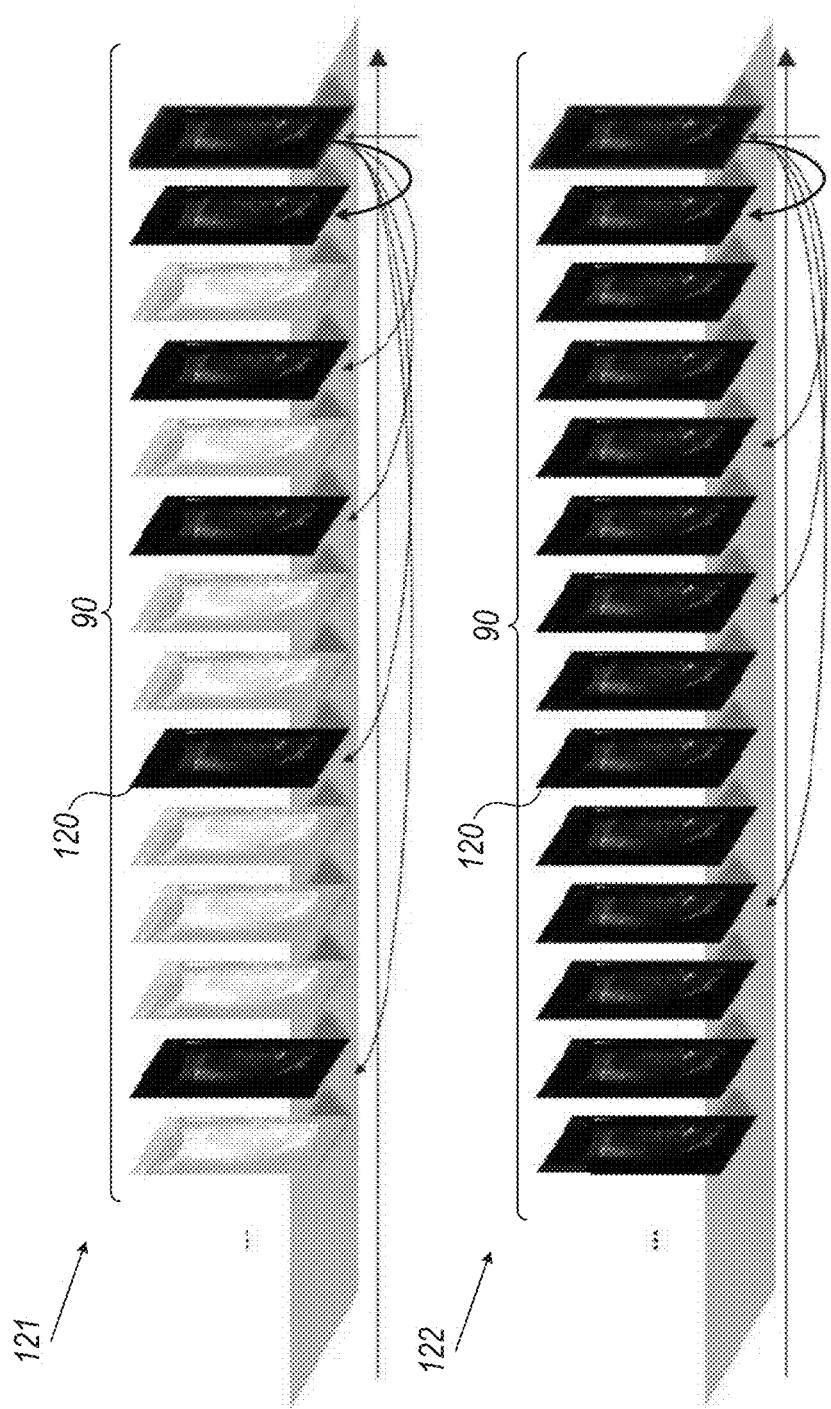
Figure 2B:
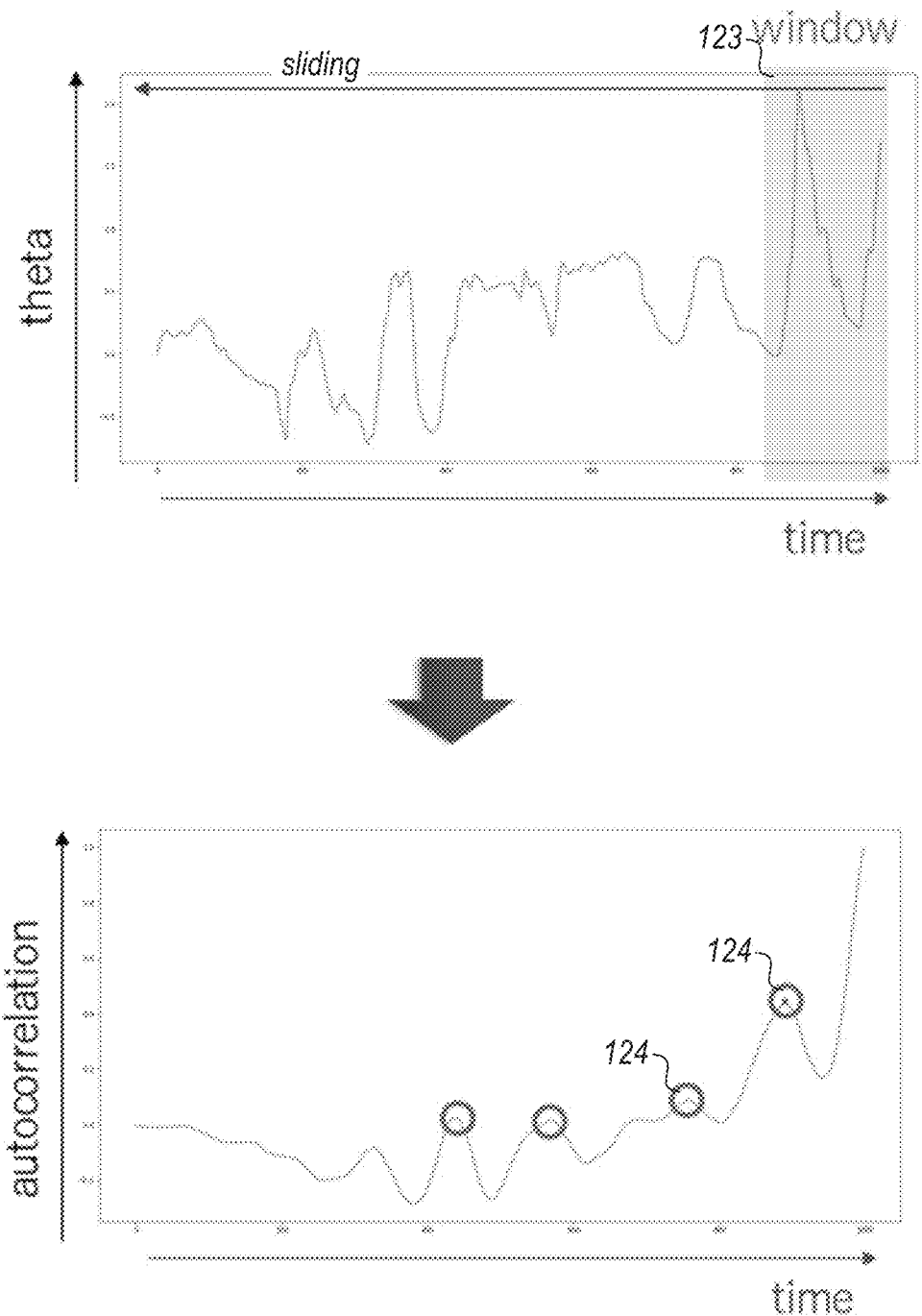

FIGS. 2A and 2B provide schematic non-limiting examples for the derivation and use of key frames, according to some embodiments of the invention.

Figure 3:
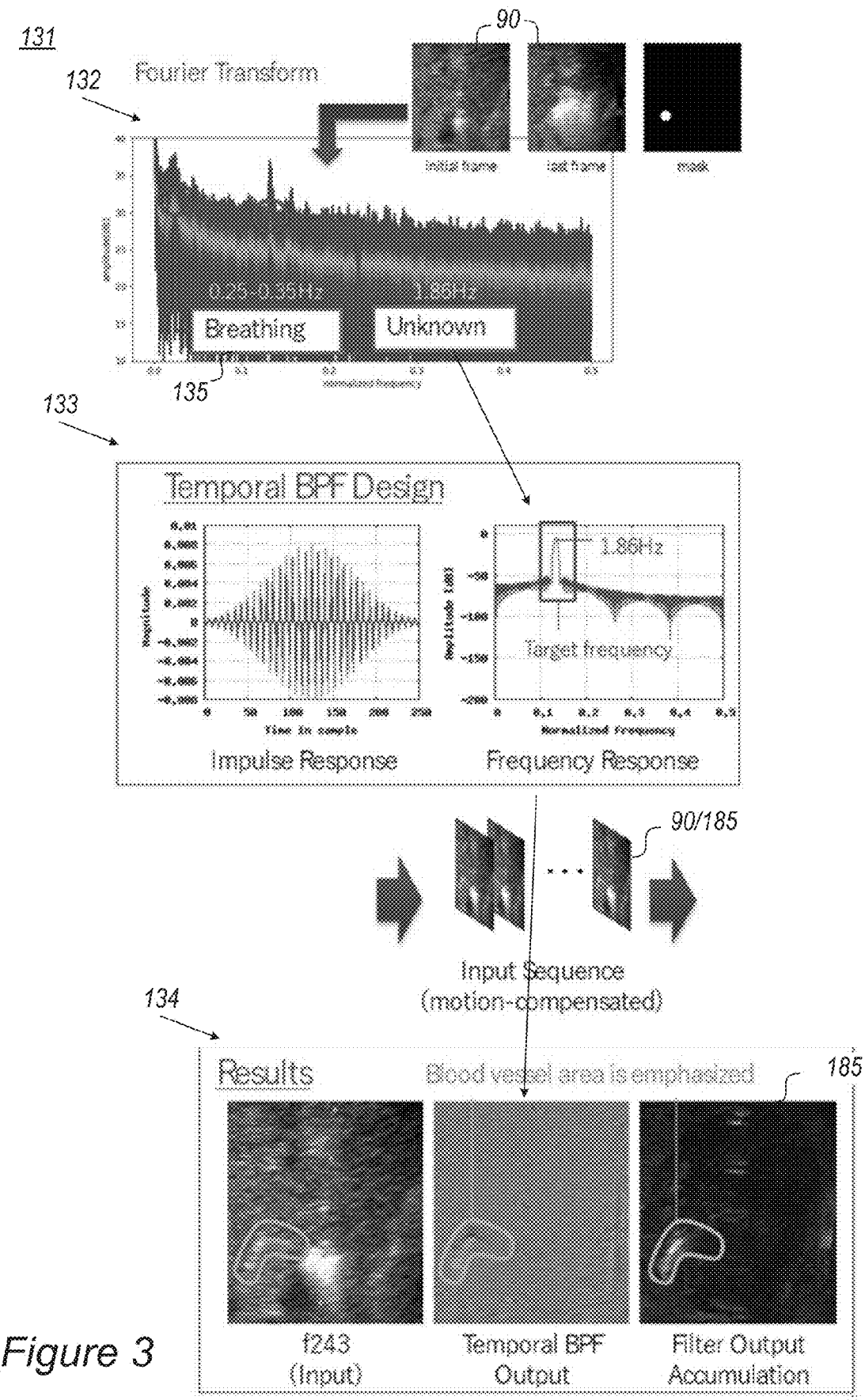

FIG. 3 provides schematic non-limiting examples for the detection of periodic changes using frequency analysis, according to some embodiments of the invention.

Figure 4:
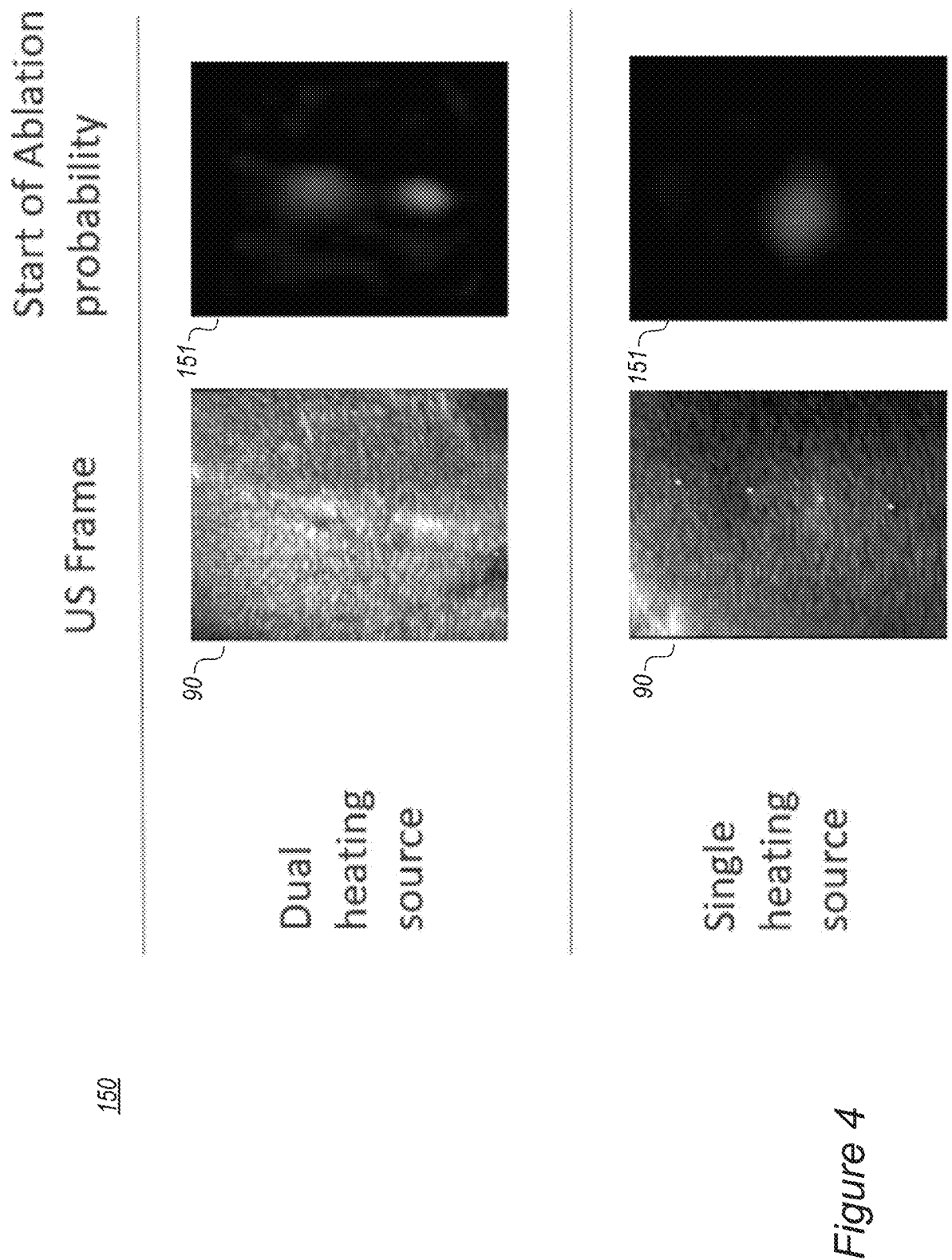

FIG. 4 provides schematic non-limiting examples for detecting the start of ablation, according to some embodiments of the invention.

Figure 5:
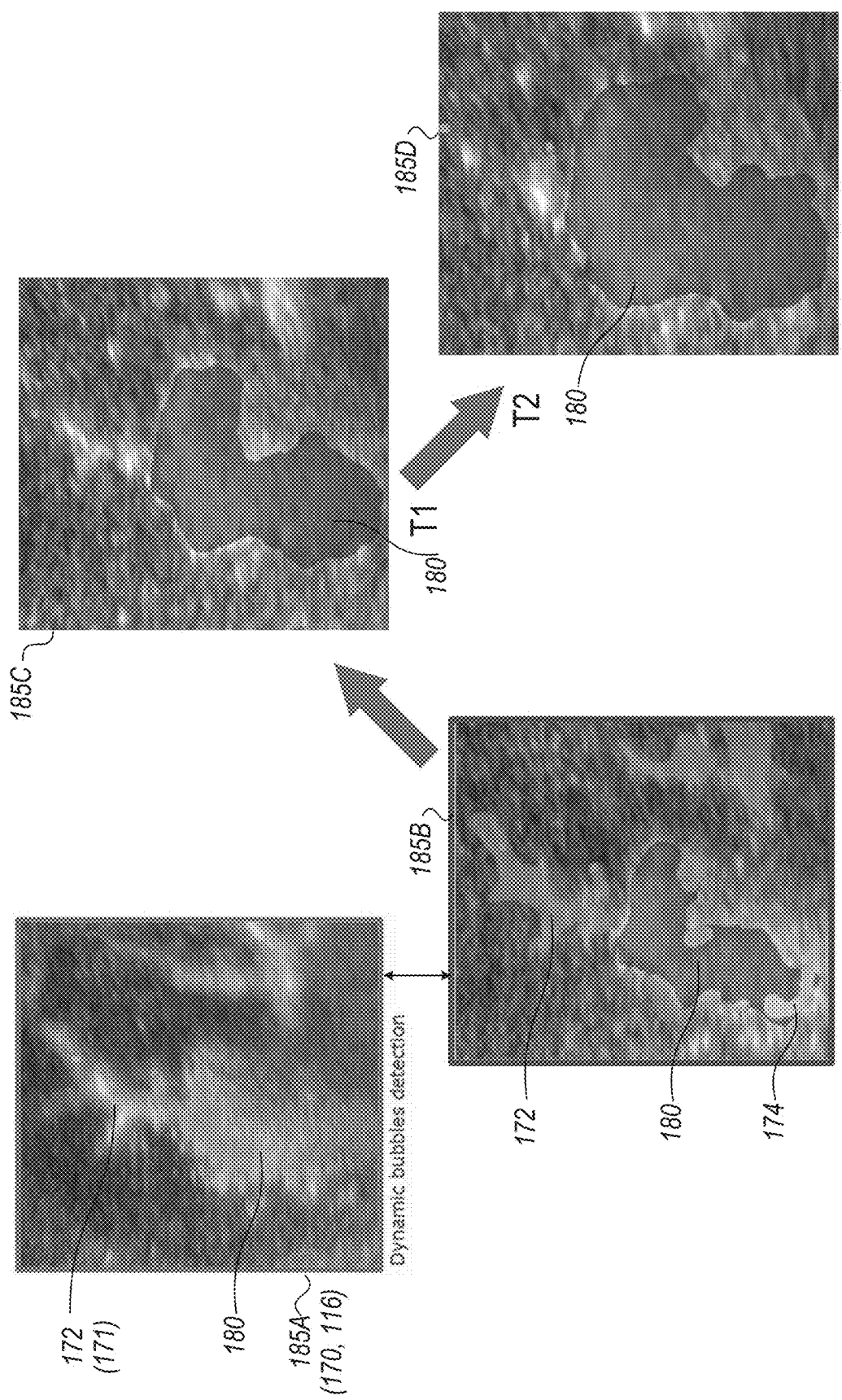

FIG. 5 provides schematic non-limiting examples for monitoring the dynamics of bubble movements, and its relation to blood vessels, according to some embodiments of the invention.

Figure 6:
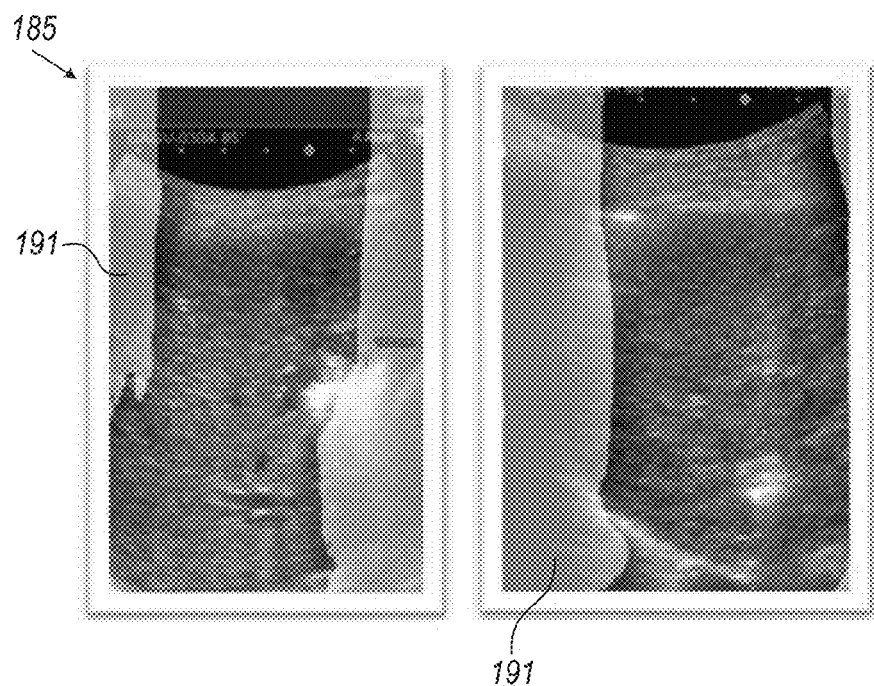
Figure 6:
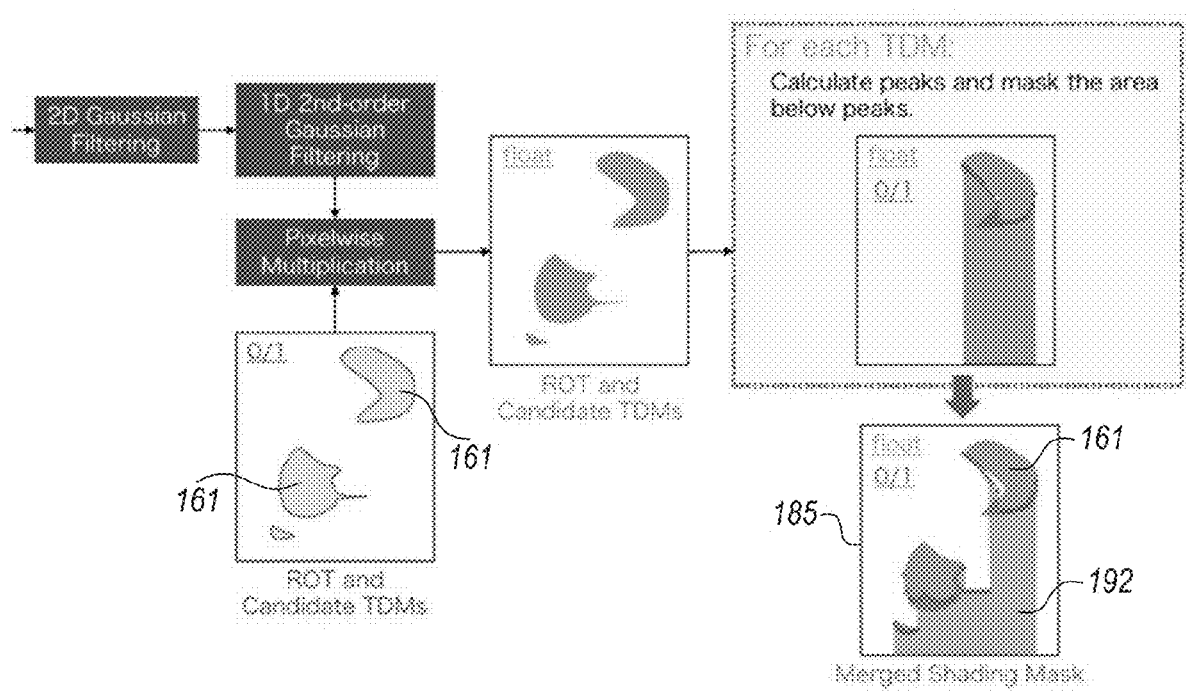

FIG. 6 provides non-limiting examples for handling shadowed regions, according to some embodiments of the invention.

Figure 7A:
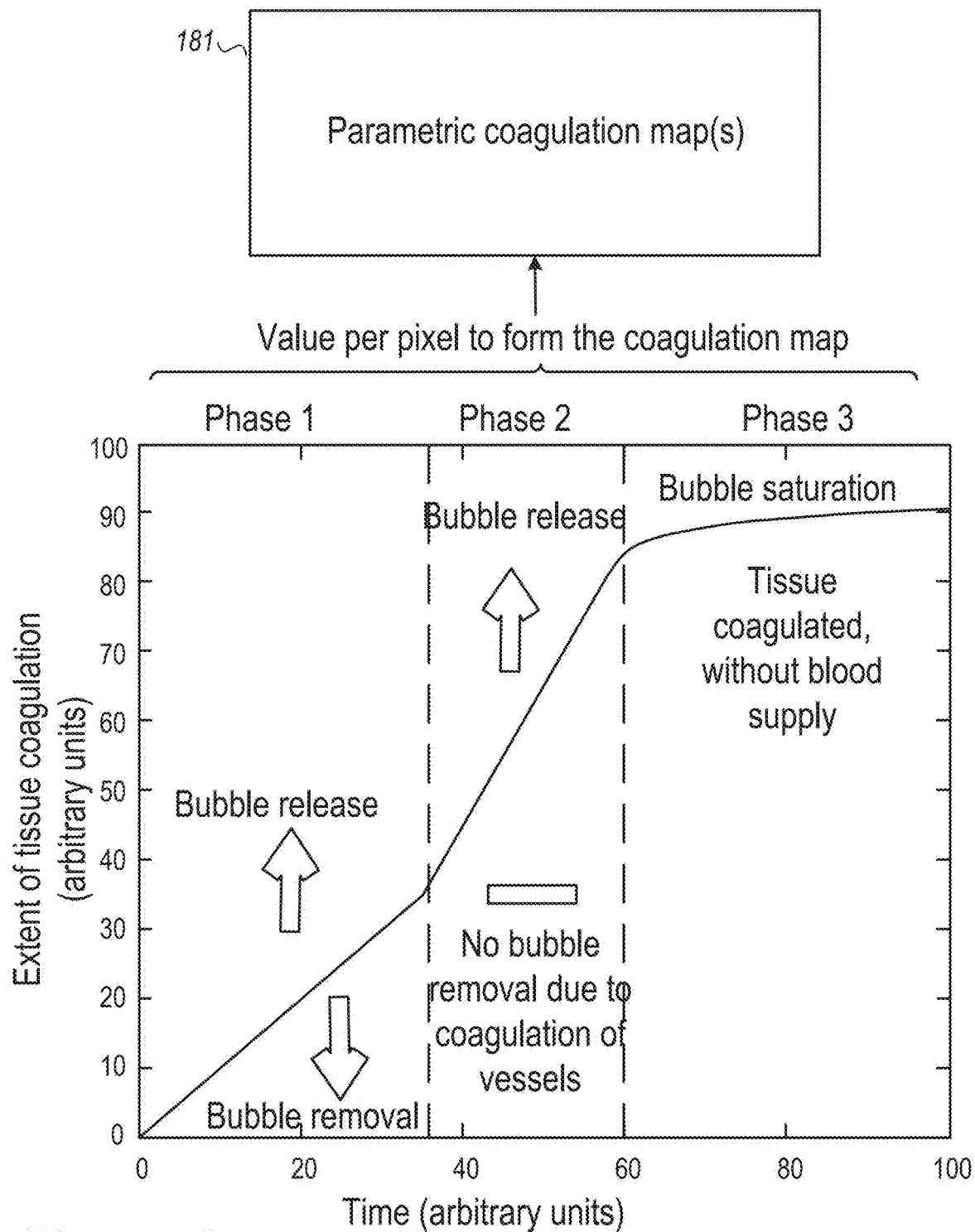

FIG. 7A is a high-level schematic illustration of a relation between bubble release and tissue coagulation, according to some embodiments of the invention.

Figure 7B:
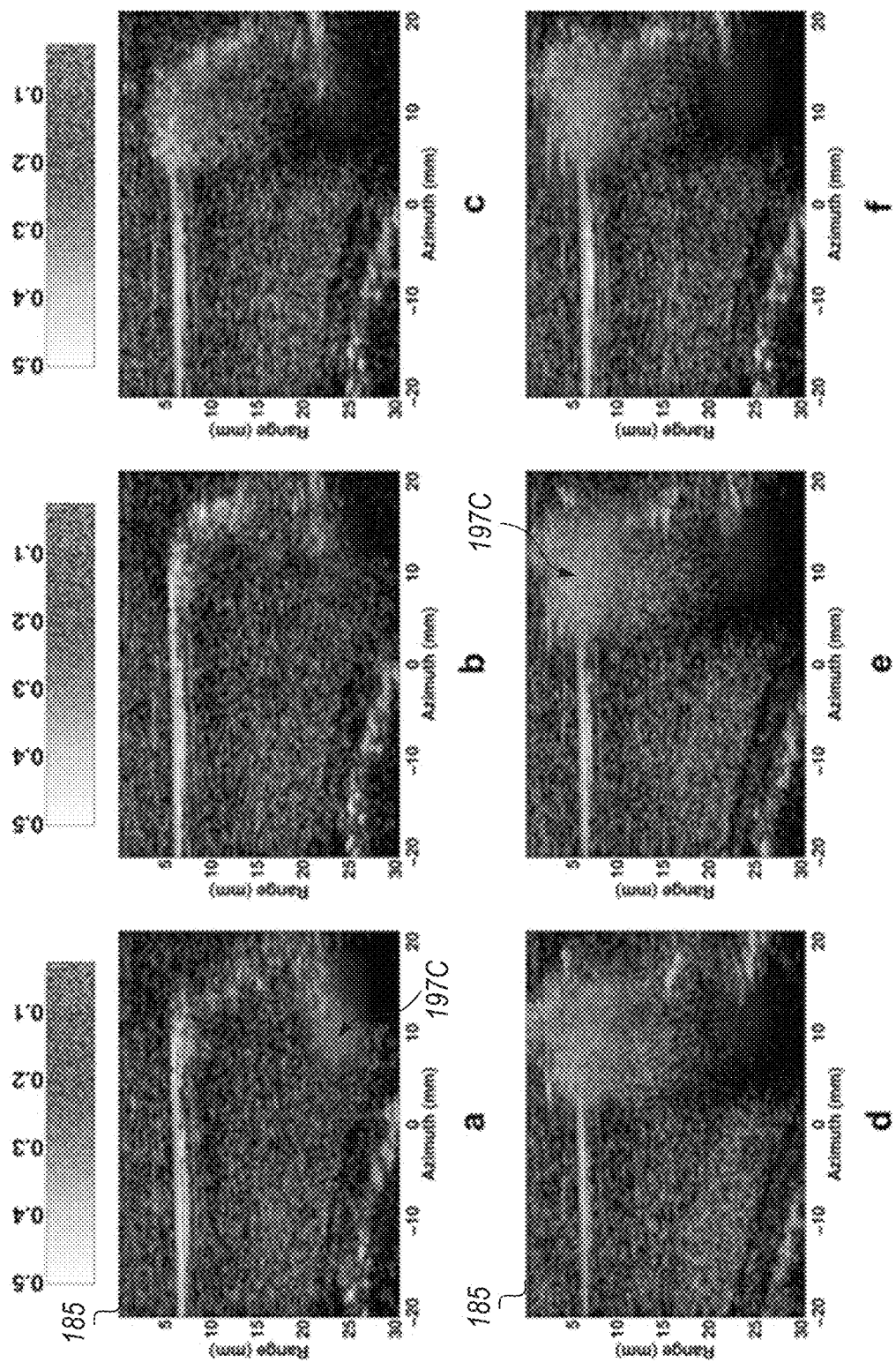

FIG. 7B is a high-level schematic illustration of a color representation of bubble development phases, according to some embodiments of the invention.

Figure 7C:
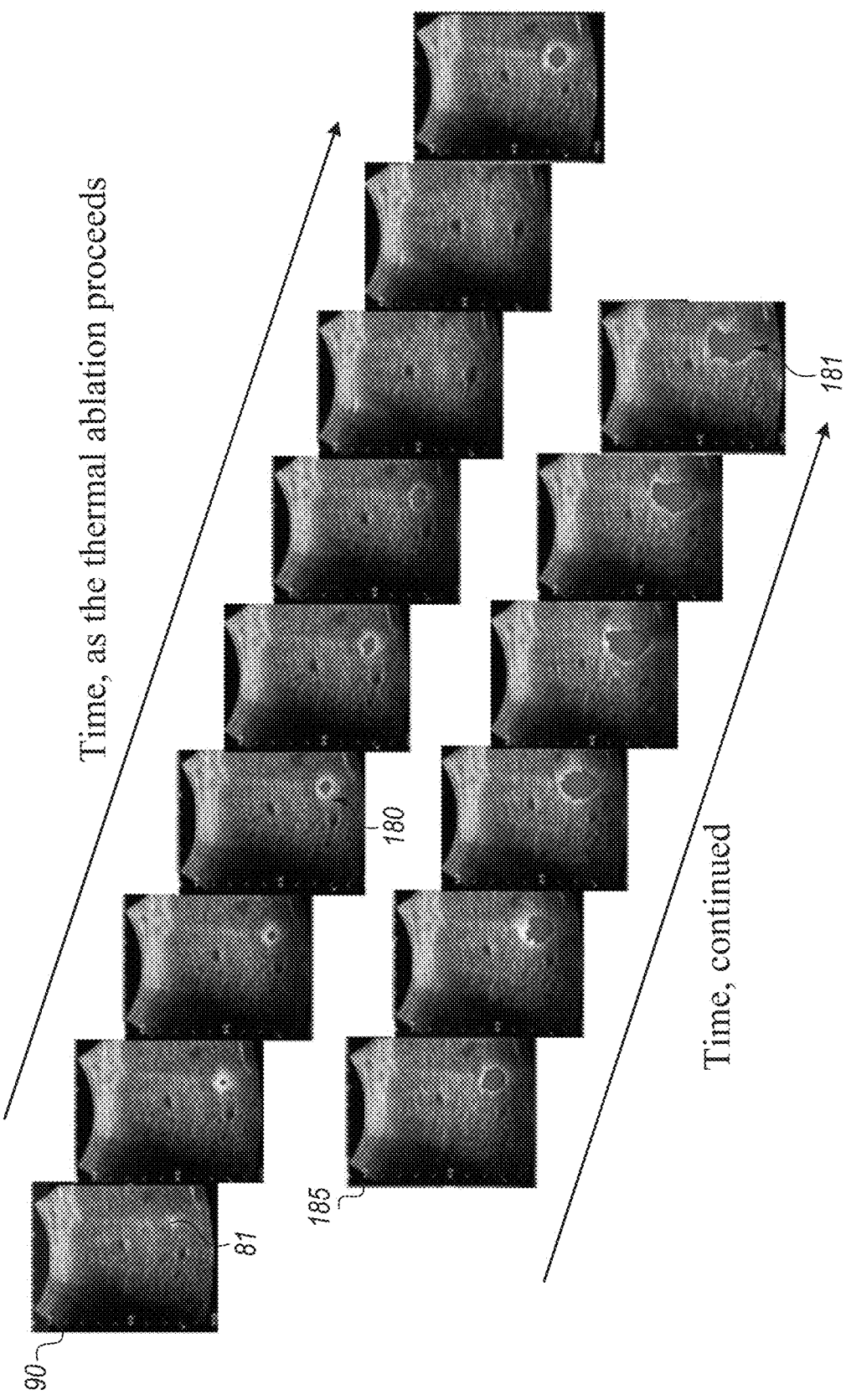

FIG. 7C is a high-level schematic illustration of sequential ultrasound images with respective demarcated damaged tissue regions, according to some embodiments of the invention.

Figure 7E:
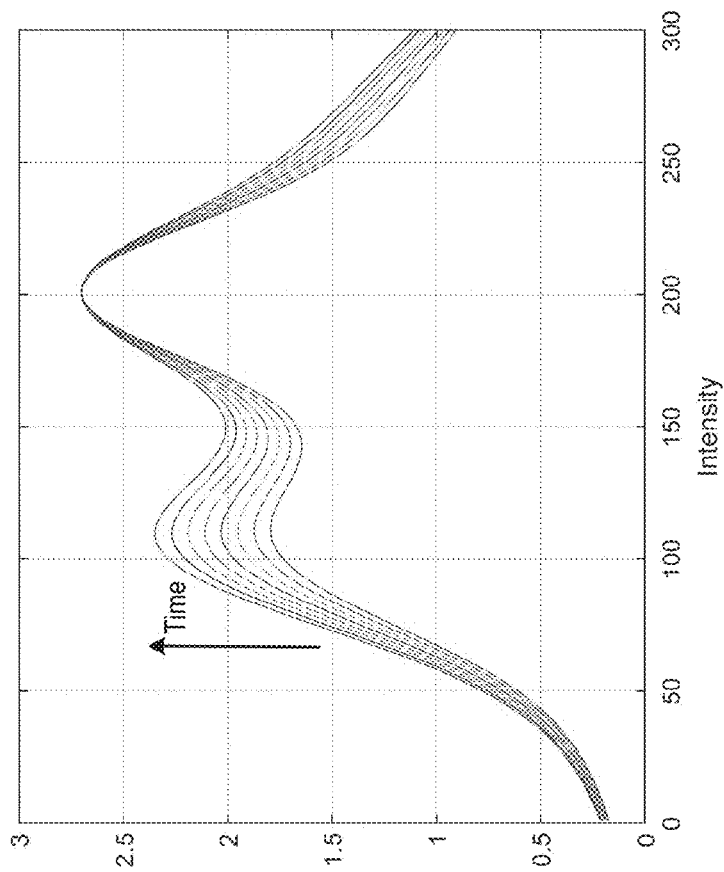
Figure 7D:
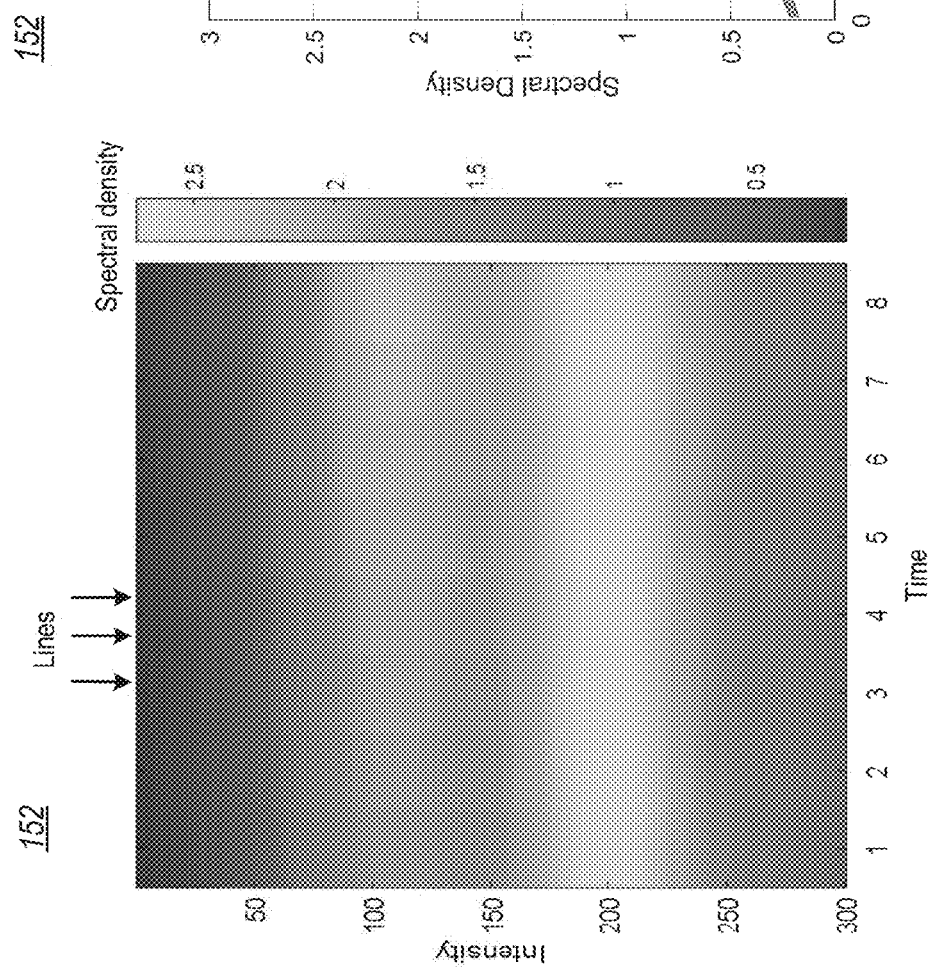

FIGS. 7D and 7E are high-level schematic examples for gray level histograms, according to some embodiments of the invention.

Figure 8A:
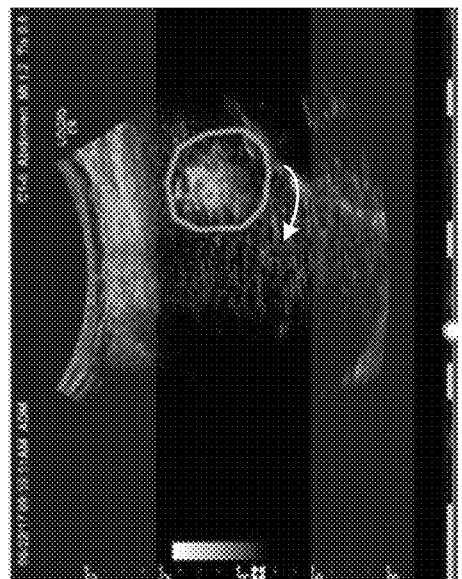
Figure 8A:
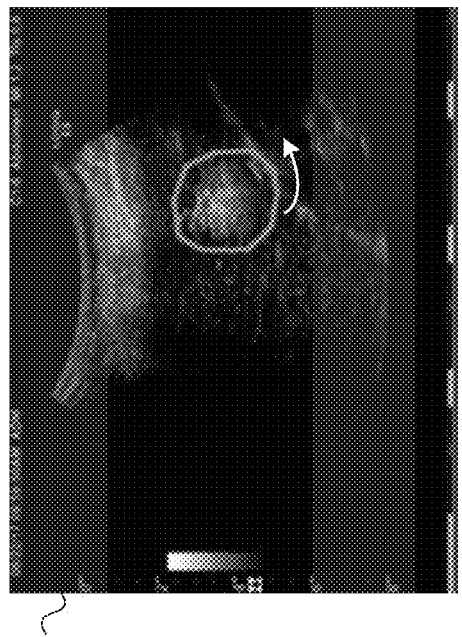
Figure 8B:
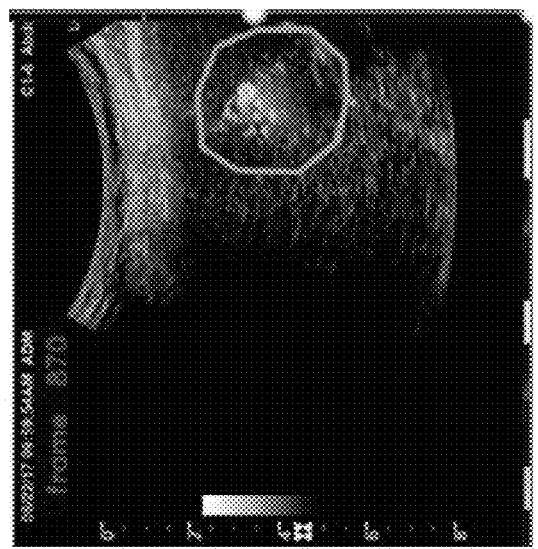
Figure 8B:
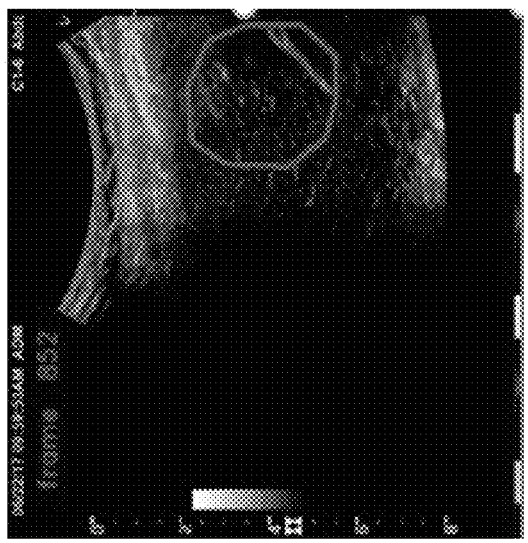
Figure 8B:
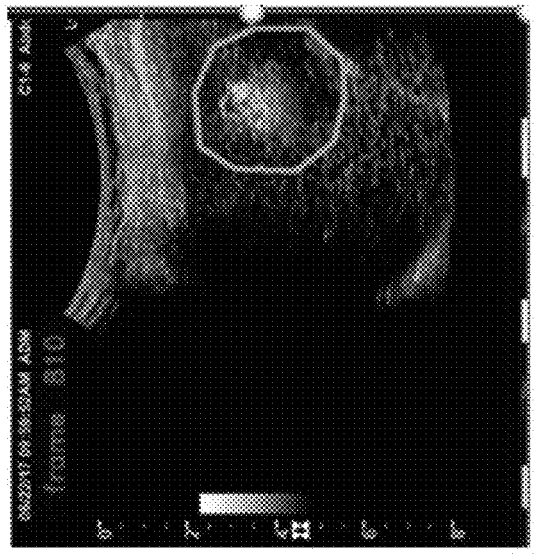

FIGS. 8A and 8B provide non-limiting examples for tracking the treated region in the enhanced ultrasound images, demonstrating the maintaining of proper registration and demonstrating tracking through movements in the images, according to some embodiments of the invention.

Figure 9A:
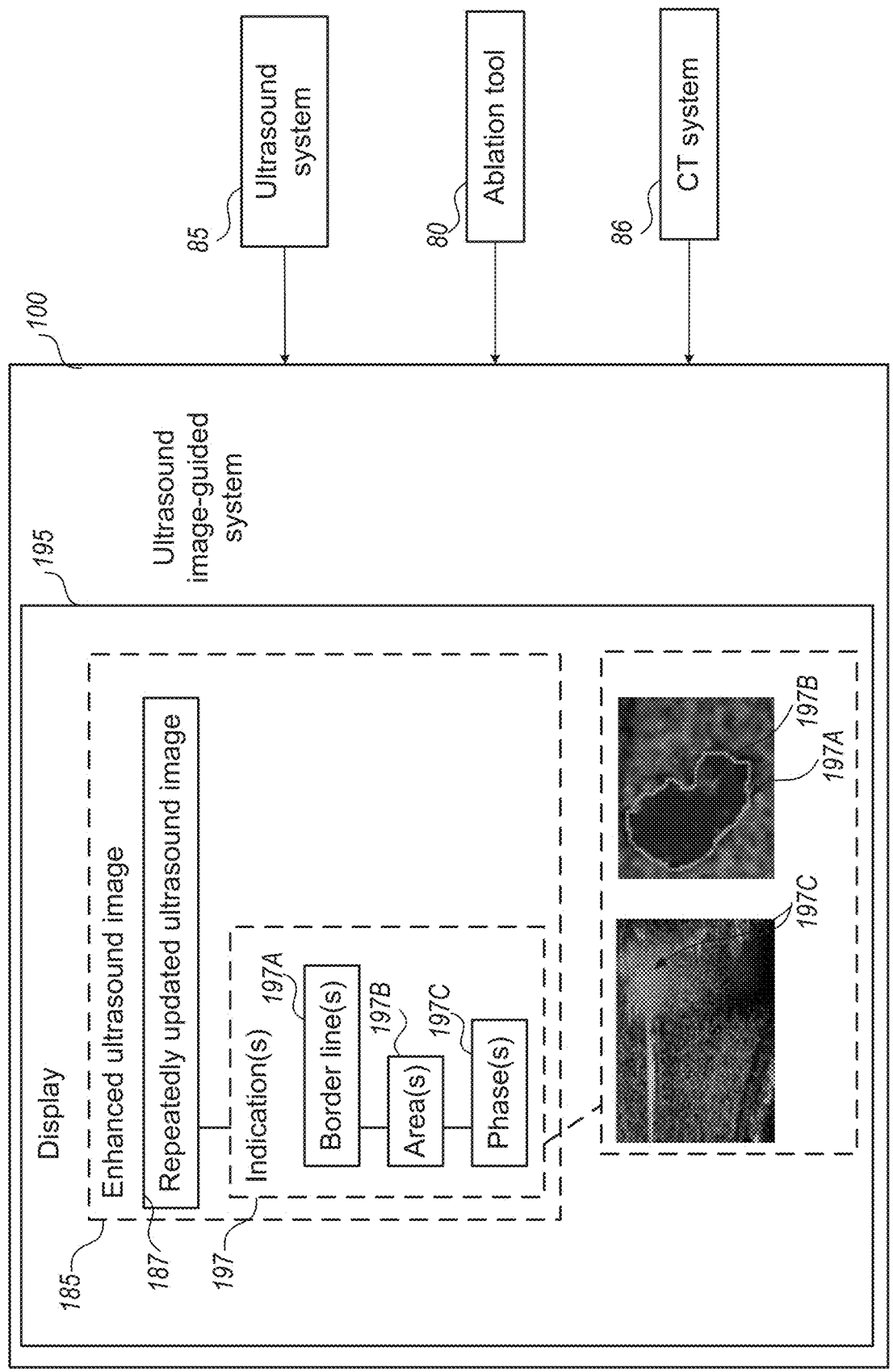

FIG. 9A is a high-level schematic illustration of an ultrasound display, according to some embodiments of the invention.

Figure 9B:
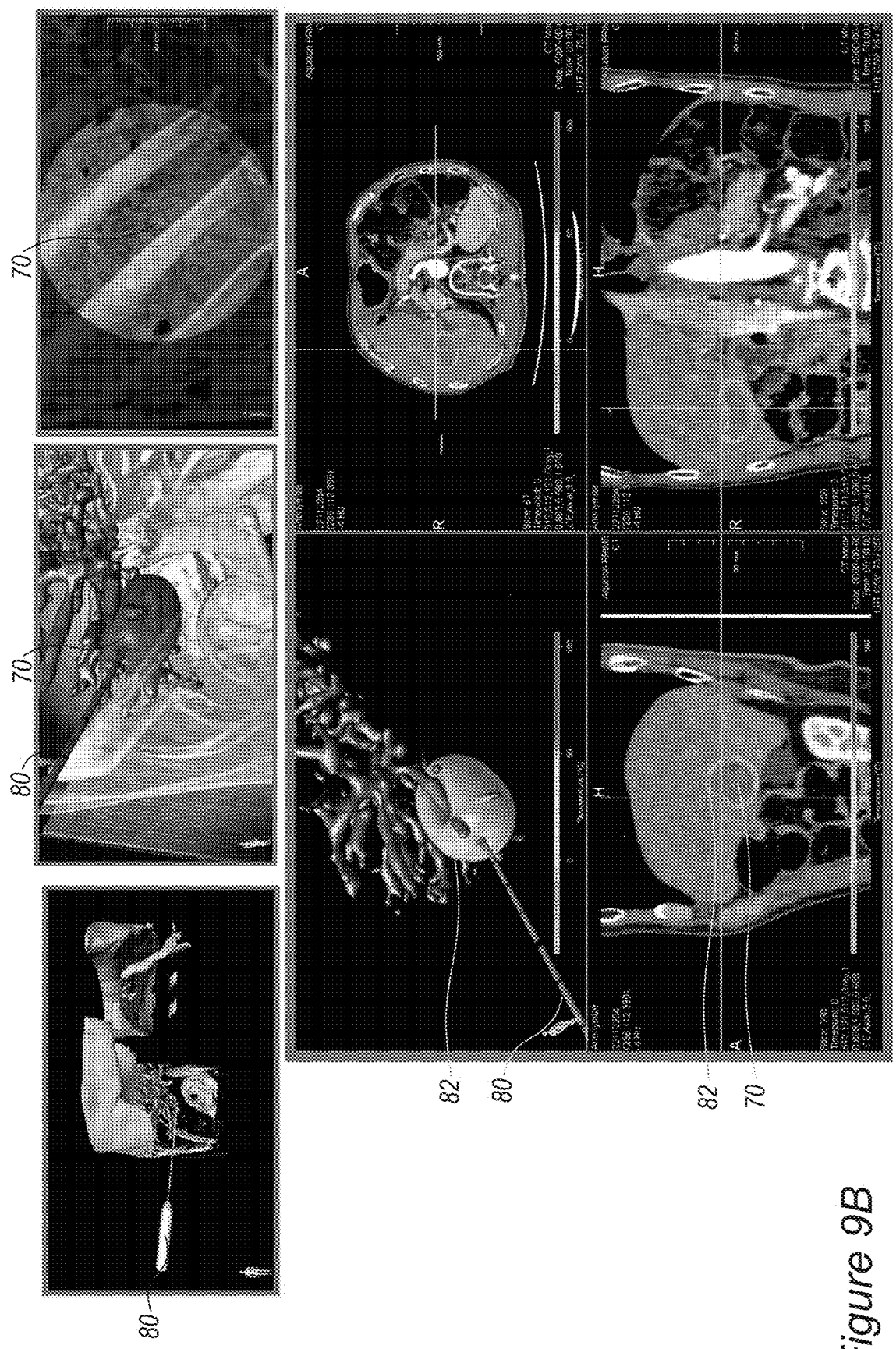

FIG. 9B is a high-level schematic illustration of CT-based image(s) and use of US images for the planning of an ablation procedure, according to some embodiments of the invention.

Figure 10:
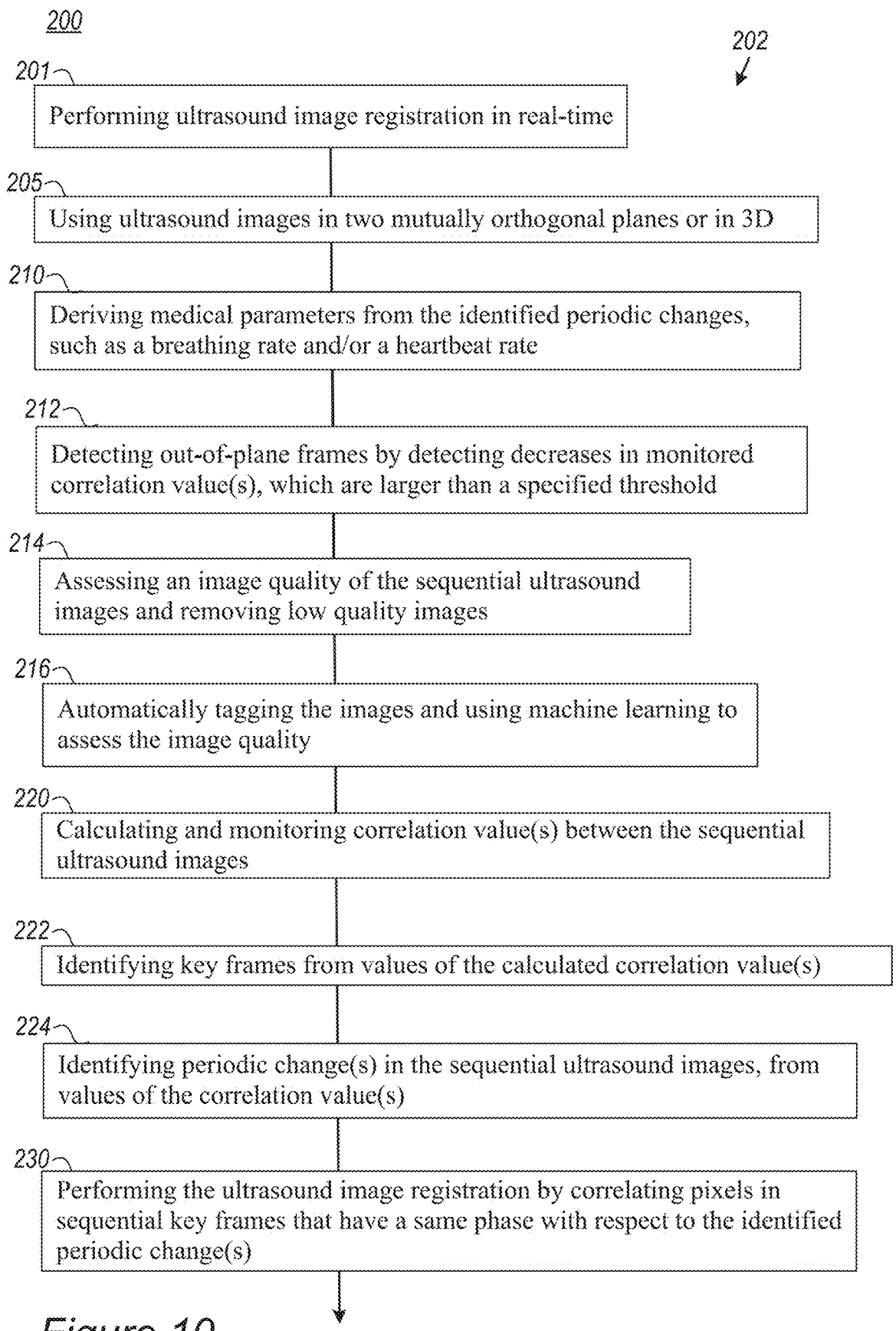

FIG. 10 is a high-level flowchart illustrating a method, according to some embodiments of the invention.

Figure 11A:
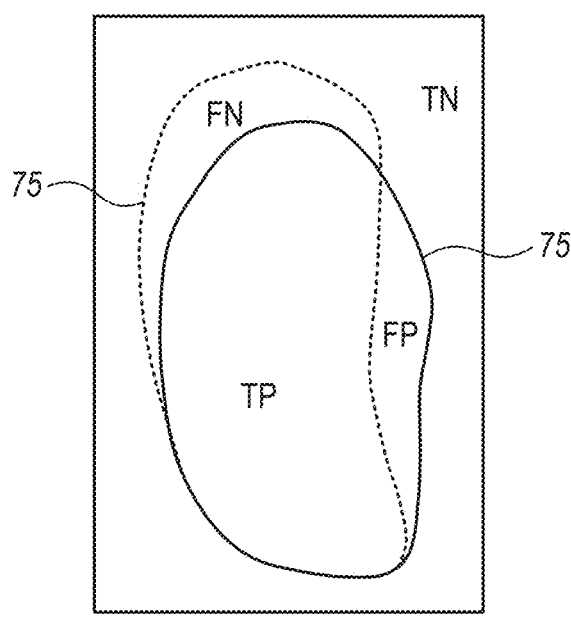
Figure 11B:
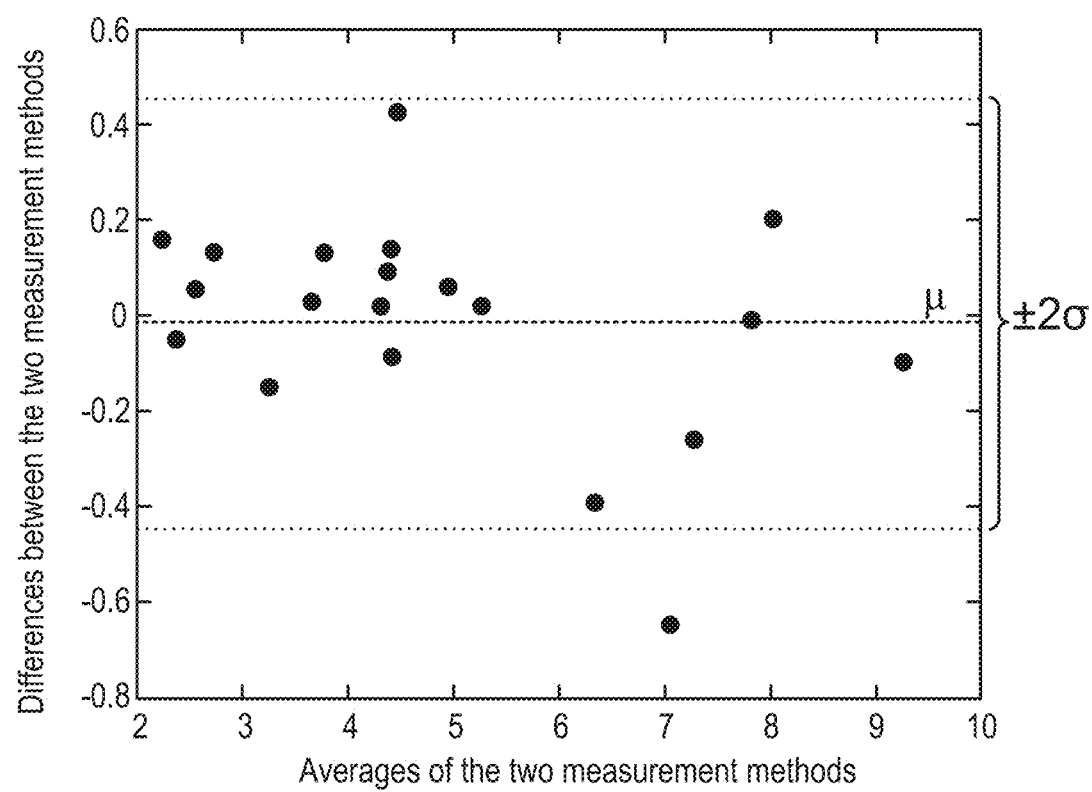
Figure 11C:
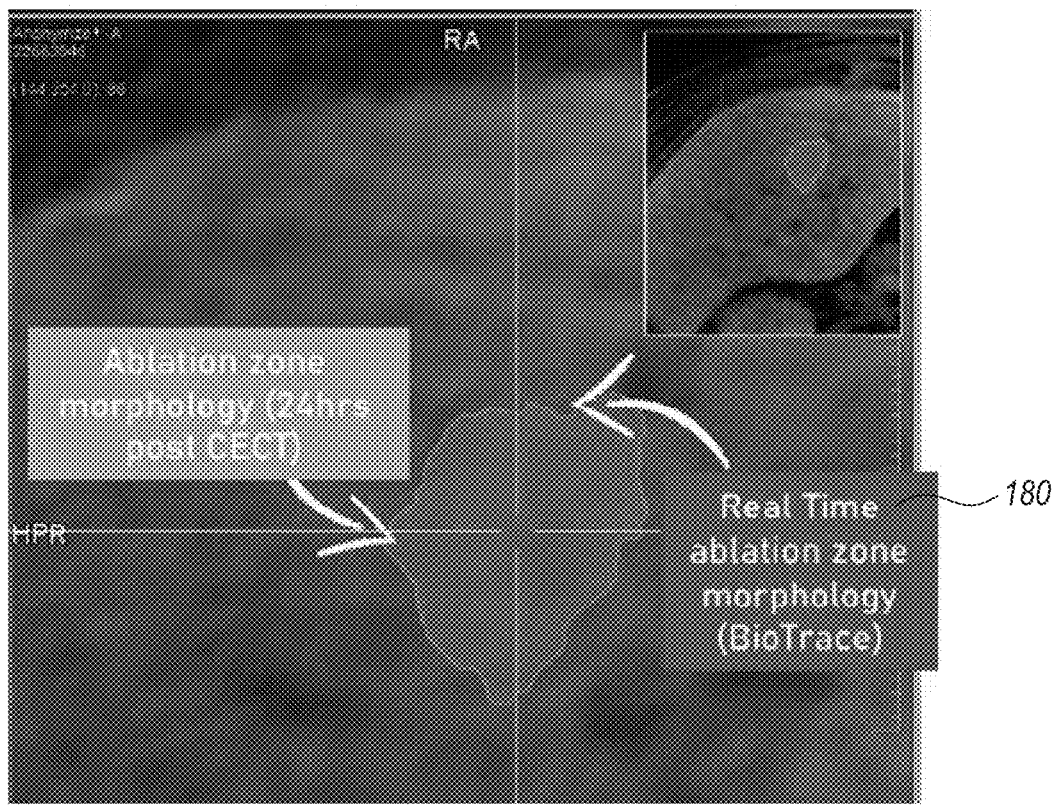

FIGS. 11A-11C provide respective illustrations of the compared damaged tissue area, a Bland-Altman plot presenting the level of similarity between demarcated damaged tissue and a comparative experimental image, according to some embodiments of the invention and damaged tissue as measured by contrast enhance CT 24 h post ablation, as measured in the prior art.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing". "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention provide efficient and economical methods and mechanisms for performing image-guided thermal ablation, e.g., of malignant tumors, specifically using ultrasound images, and thereby provide improvements to the technological field of medical ablation and ultrasound image processing. Image-guided, malignant tumor thermal ablation (IGA) is gradually becoming the first line of treatment and is being applied in a large variety of clinical settings as a viable alternative to tumor resection in open surgery. Disclosed IGA methods, at least on some embodiments, are configured to provide cell-lethal ablation zones with clinically effective margins and minimal collateral damage, that are at least equivalent to open surgery results.

Disclosed embodiments provide improvements and/or solution to any of the typical four phases of effective IGA treatments, including pretreatment imaging, pretreatment planning, and in particular on-line monitored tumor ablation and post-treatment evaluation. Moreover, in case of feasible percutaneous tumor ablation procedures in which the tumor is accessible percutaneously, disclosed embodiments provide pretreatment imaging and planning and in particular controllable thermal ablation of the tumor that avoids damage to adjacent tissues and furthermore allows the treating personnel to visualize, verify and validate treatment response non-invasively and possibly in real-time. Particularly in contrast to prior art methods that typically require waiting a day for imaging feedback concerning the damages tissues, disclosed real-time or near-real-time feedback allows accurate, complete and verifiable thermal ablation of tumors. Advantageously with respect to prior art attempts to monitor ablation, disclosed embodiments follow the tissue's biological signature, namely the typical ways the tissue reacts to the thermal ablation, to quantify the ablation damage.

Systems, displays and methods are provided, for performing ultrasound image registration and for using ultrasound images to guide thermal ablation. Registration is carried out by calculating and correlating sequential ultrasound images, identifying key frames from the correlation values, identifying periodic change(s) corresponding to breathing and heart beating, and correlating pixels in sequential key frames that have a same phase with respect to the identifying periodic change(s). Based on the registration, the start of ablation is detected, bubbles formed in the ablation procedure are identified and their movements are followed—all using B-mode ultrasound images only. Using the identified bubbles, the thermally damaged tissue region is demarcated and provided in real-time—at an accuracy similar to prior art post-ablation results. Disclosed systems and methods therefore provide the physician with an ultrasound-based way of monitoring thermal ablation in real-time. Disclosed systems and methods therefore provide the physician with an ultrasound-based way of monitoring thermal ablation in real-time. Additional features include ultrasound image quality assessment, safety alerts, ablation analysis as well as simulation and planning of ablation procedures.

FIGS. 1A-1E are high-level schematic block diagrams of an ultrasound image-guided system 100 for thermal ablation, according to some embodiments of the invention.

Figure 1A:
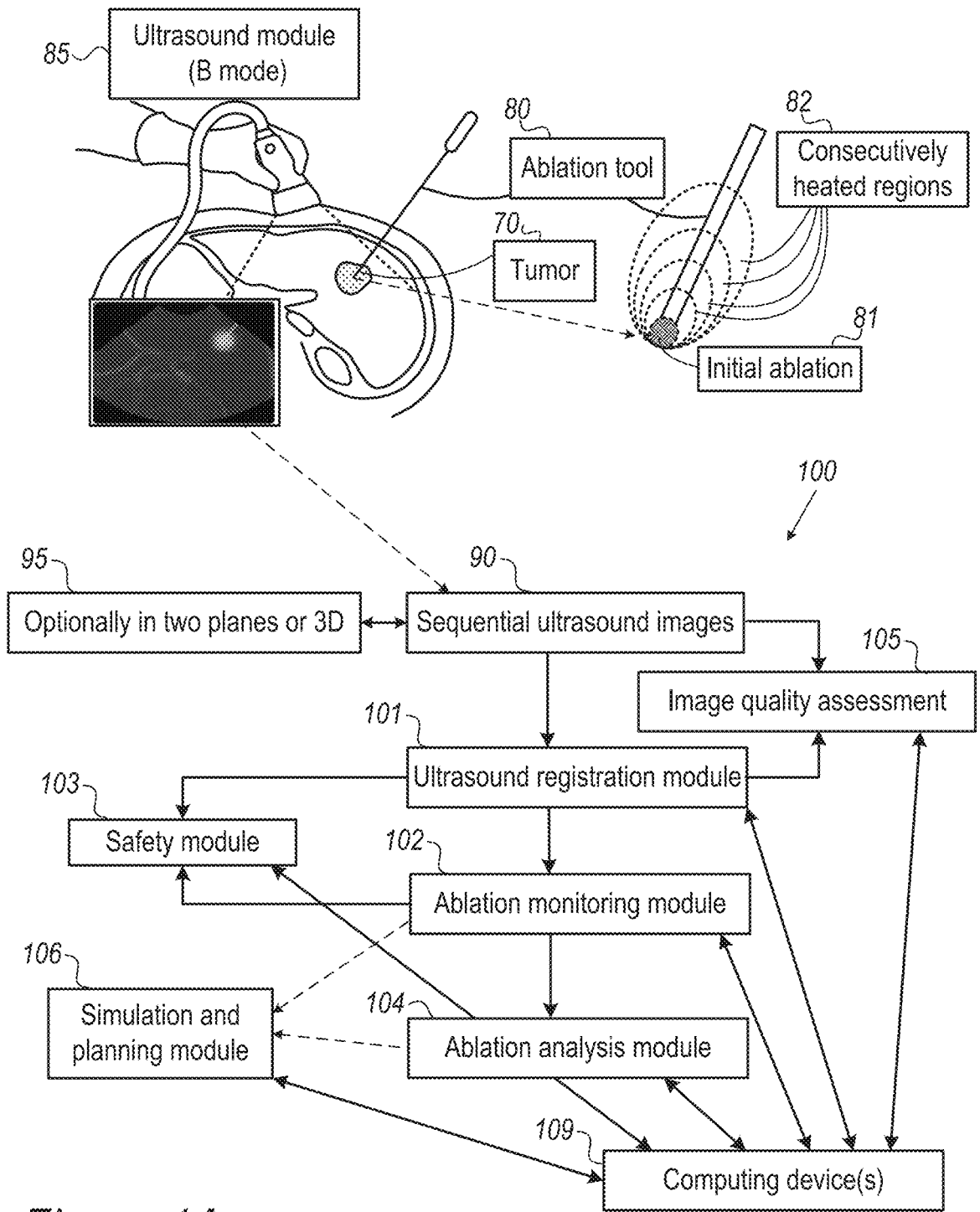
Figure 1B:
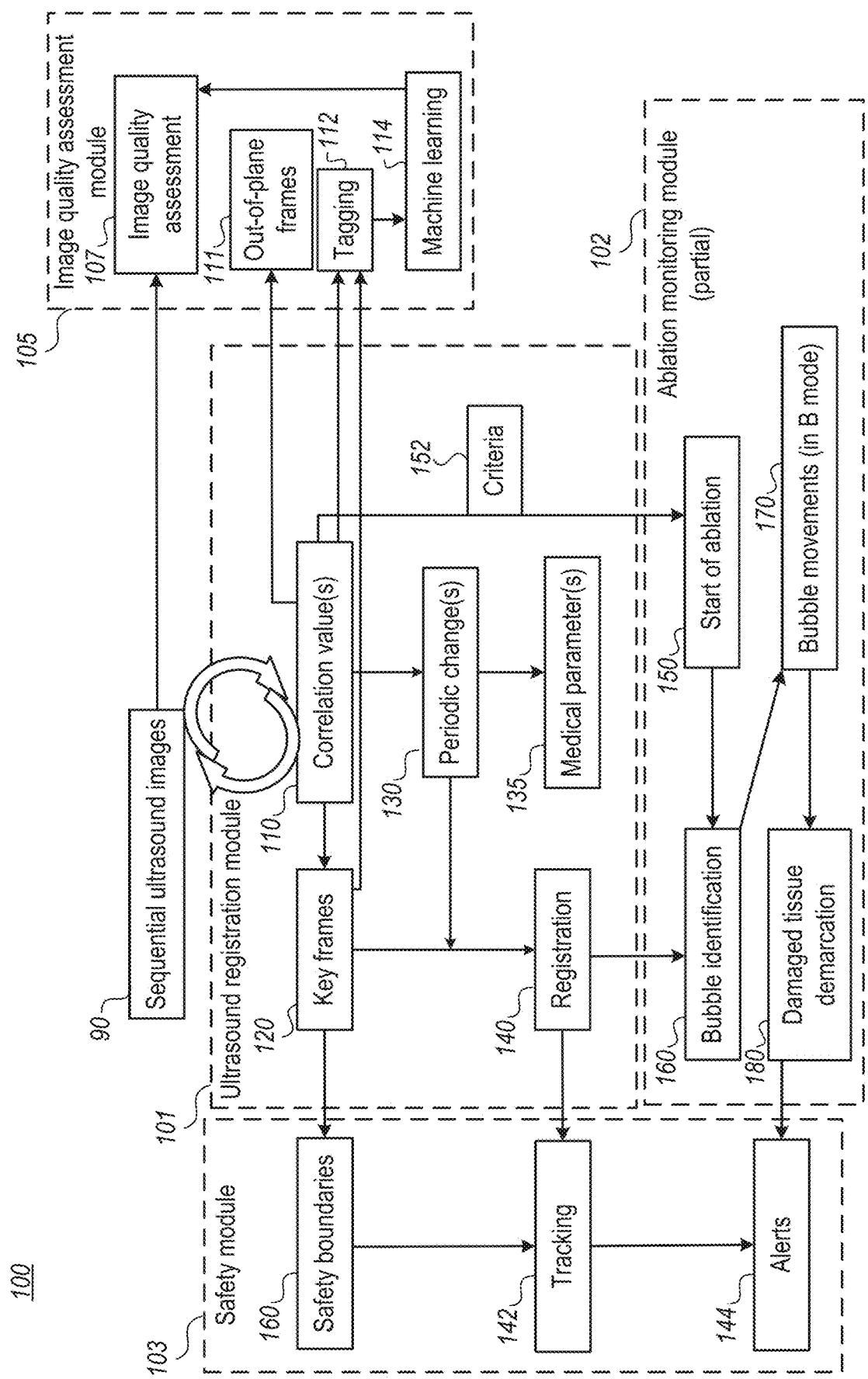
Figure 1C:
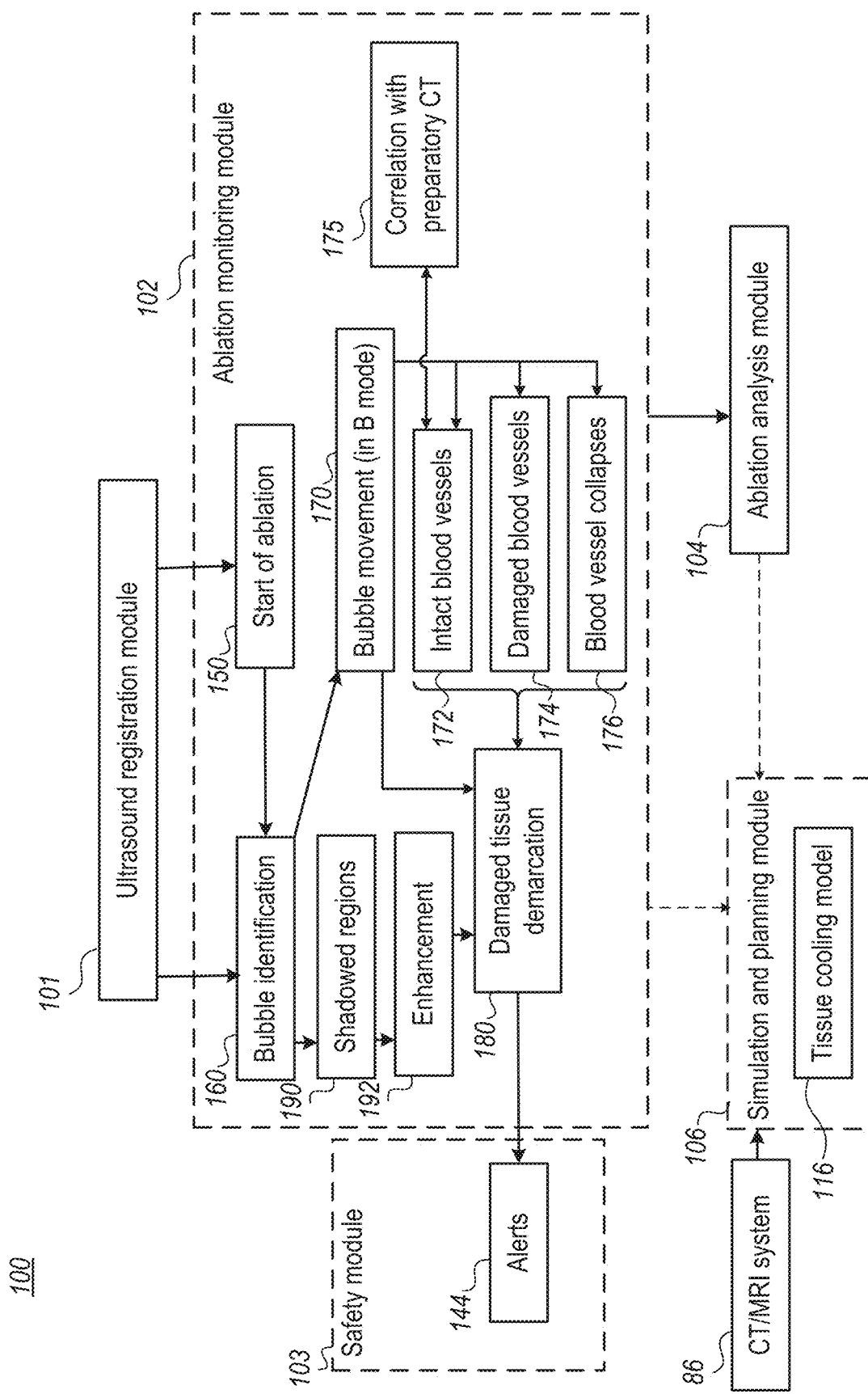
Figure 1D:
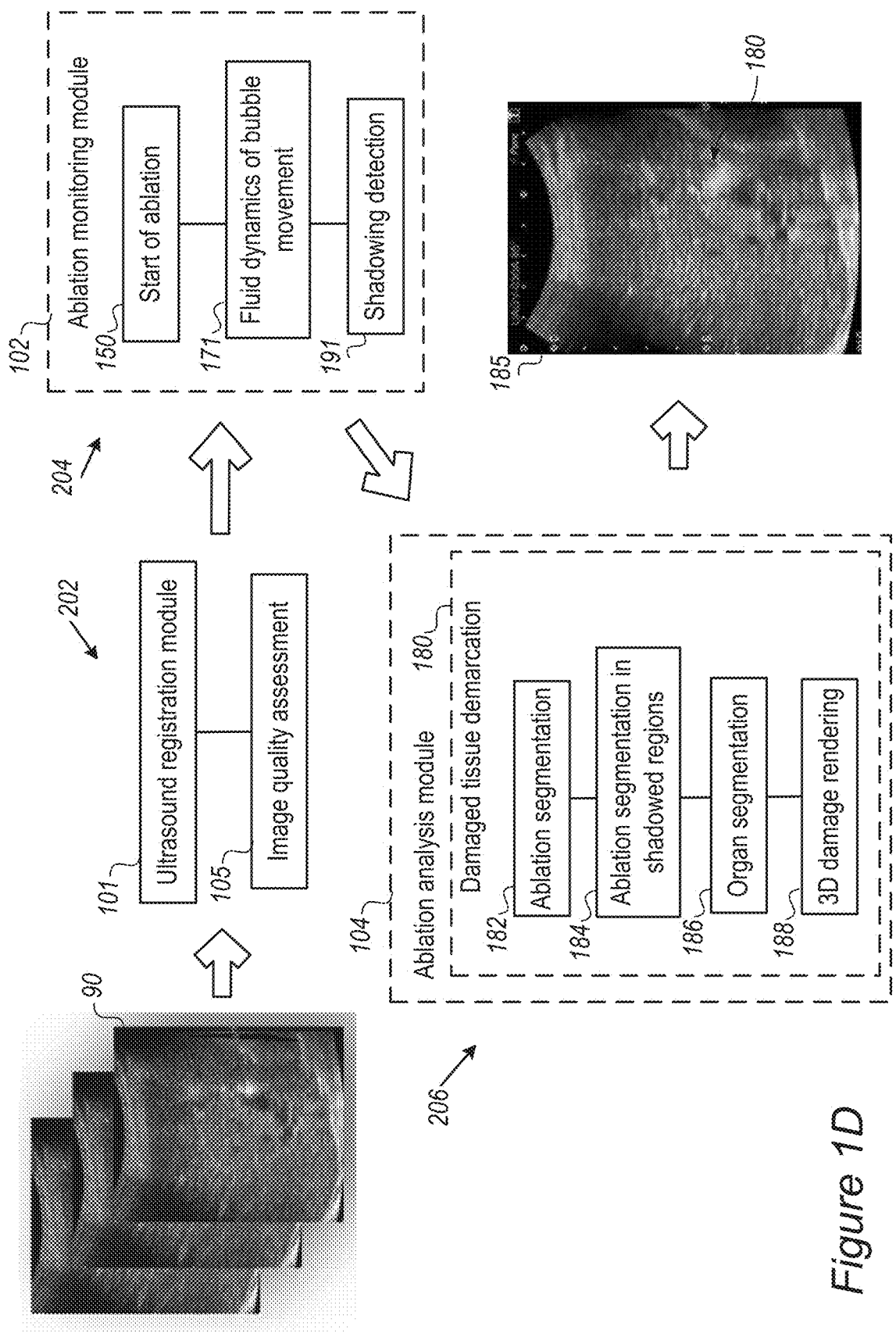
Figure 1E:
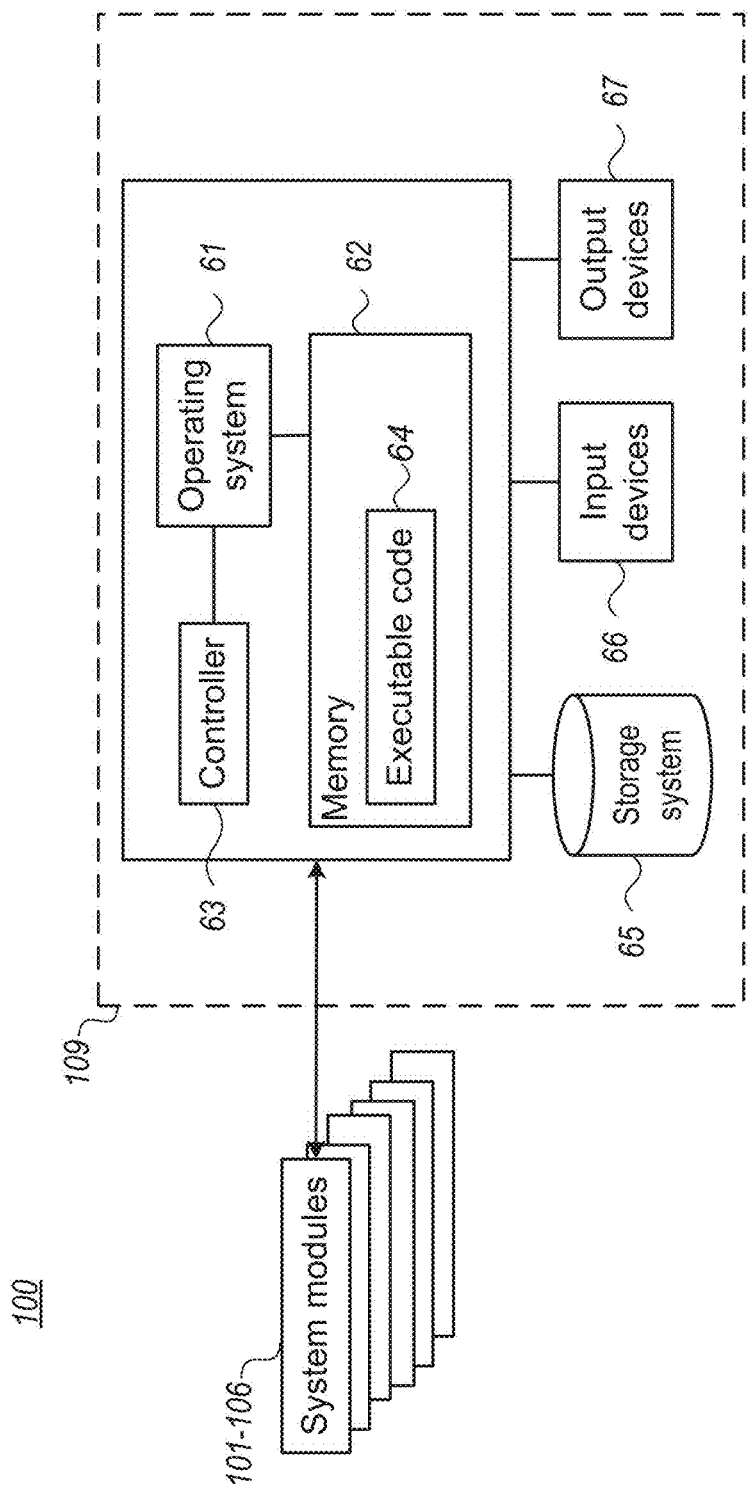

FIG. 1A illustrates schematically a thermal ablation procedure performed using a thermal ablation tool 80 and modules of system 100. FIG. 1B illustrates schematically details of an ultrasound registration module 101 in system 100, as well as a safety module 103 and an image quality assessment module 105, and FIG. 1C illustrates schematically details of ablation monitoring module 102 of system 100. The separation of system operation into module is schematic and non-limiting, and is intended merely for explanatory purposes. FIG. 1D illustrates schematically an algorithm flow for estimating liver tissue damage, according to some embodiments of the invention. FIG. 1E illustrates schematically computing device 109 that is described below.

FIG. 1A illustrates schematically a thermal ablation procedure performed using thermal ablation tool 80, e.g., using RF or possibly laser energy, to ablate tissue 70 such as a tumor, e.g., in the liver. The thermal ablation procedure is monitored in real-time by an ultrasound module 85, operating in B mode, which provides sequential ultrasound images 90 which are used by ultrasound image-guided system 100 to monitor the thermal ablation procedure, e.g., identifying ablated tissue, distinguishing targeted tissue 70 from surrounding tissue, providing feedback concerning the progression of the thermal ablation procedure, indicating the extent of removed targeted tissue 70, alerting concerning ablated surrounding tissue and/or safety boundaries being approached, as well as providing real-time assessment of the success of the thermal ablation procedure in removing targeted tissue 70. It is noted that in current technology, a time period of about a day is required to pass before reliable imaging can be used to determine the extent of ablated targeted tissue 70 and damage to surrounding tissue, by then another procedure should be undertaken to correct for any deficiencies. In disclosed embodiments, the provided feedback is immediate and allowed for optimization of the thermal ablation procedure during its execution.

In various embodiments, ultrasound image-guided system 100 for thermal ablation includes ultrasound registration module 101 configured to provide continuity and spatial orientation from incoming sequential ultrasound images 90 and ablation monitoring module 102 configured to detect and monitor the thermal ablation procedure. Additional modules may be used to provide safety alerts (e.g., safety module 103), assess image quality (e.g., image quality assessment module 105) and possibly improve image quality, provide reports concerning the thermal ablation procedure after it is finished, derive additional data and analysis (e.g., ablation analysis module 104) etc., and to plan the thermal ablation procedure (e.g., simulation and planning module 106).

Ultrasound registration module 101 (see, e.g., FIG. 1B) may be configured to calculate and monitor at least one correlation value 110 between received sequential ultrasound images 90, identify a plurality of key frames 120 from calculated correlation value(s) 110, identify at least one periodic change 130 in sequential ultrasound images 90, from values of calculated correlation value(s) 110, and perform ultrasound image registration 140 by correlating pixels in sequential key frames 120 that have a same phase with respect to the identifying periodic change(s) 130.

FIGS. 2A and 2B provide schematic non-limiting examples for the derivation and use of key frames 120, according to some embodiments of the invention. Key frames 120 may be grouped in a keyframe bank 121, comprising, e.g., few, tens or hundreds of key frames 120, to which incoming images 90 may be compared. For example, incoming images 90 may be compared to last and previous key frames, based on image features and their periodicity with respect to periodic changes 130. For example, motion parameters autocorrelation may be used to select key frames 120 from keyframe bank 121 with respect to incoming images 90. Switching used key frames 120 may be configured to overcome drift issues. In certain embodiments, a model of predicting motion parameters (e.g., a velocity model) may be applied for the selection of key frames 120, possibly as a starting point for applying enhanced correlation coefficient (ECC) maximization.

In certain embodiments, a circular frame buffer 122 may comprise hundreds or thousands of consecutive frames, which represent one or more cycles of periodic changes 130. Incoming images 90 may be compared to last and arbitrary frames within circular frame buffer 122, based on image features and their periodicity with respect to periodic changes 130.

FIG. 2B provides schematic non-limiting examples for the detection of periodic changes 130 and implementing the key frame selection, according to some embodiments of the invention. In certain embodiments, key frames 120 may be selected from frame buffer 121 using autocorrelation of motion parameters, calculated, e.g., using a fixed size of sliding window 123 correlated to the past. FIG. 2B provides an example of sliding window 123 (sliding back with respect to time) applied to Pearson's $\theta$ over time and the resulting autocorrelation values over time. Time points 124 provide the peaks of the autocorrelation—indicating the periodicities of periodic changes 130. Clearly, alternative methods of detecting periodicity may be applied to the image data or parts thereof (e.g., periodicity may be detected in specific portions of images, relating e.g., to blood vessels, treated regions or other portions of the images).

In certain embodiments, ultrasound registration module 101 may be configured to perform ultrasound image registration 140 in real-time with respect to received sequential ultrasound images 90. Real-time registration 140 may be carried out during the performance of the thermal ablation procedure, possibly with a slight delay required to carry out the image processing procedures and depending on the technical implementation of the ultrasound registration module 101, ultrasound image quality, proficiency of the ultrasound operator, etc. The term "real-time" is used herein to denote no delay, delays of few milliseconds (e.g., 1-5 msec, 5-10 msec, or any intermediate ranges), delays of tens of milliseconds (e.g., 10-50 msec, 50-100 msec, or any intermediate ranges), delays of hundreds of milliseconds (e.g., 100-500 msec, 500-1000 msec, or any intermediate ranges), or up to delays of few seconds (e.g., 1-5 sec or any intermediate ranges)—between the capturing of the ultrasound images and their registration 140.

Ultrasound registration module 101 may be configured to process ultrasound images 90 with respect to the type of ultrasound imaging module 85. In various embodiments, ultrasound registration module 101 may further comprise, and be adjusted to the type of, ultrasound imaging module 85. In various embodiments, ultrasound registration module 101 and ultrasound imaging module 85 may be partly or fully integrated.

In certain embodiments, ultrasound registration module 101 may be configured to derive medical parameters 135, such as a breathing rate and/or a heartbeat rate and/or indicate patient movements, from the identified periodic change(s) 130. For example, medical parameters 135 may be derived from a frequency analysis 131 of ultrasound images 90 and/or of specified regions thereof. Identified frequencies (of periodic changes 130) may be used to monitoring medical parameters 135 such as heart and breathing rates, and also to enhance blood vessel detection 172, 174 and/or bubble movements 170 through blood vessels.

FIG. 3 provides schematic non-limiting examples for the detection of periodic changes 130 using frequency analysis 131, according to some embodiments of the invention. Frequency analysis 131 may comprising applying a Fourier transform 132 to a sequence of images 90 (and/or image parts, e.g., using a mask) and detecting prominent frequencies. In the illustrated non-limiting example, prominent frequencies of 0.25-0.35 Hz may be related to the breathing rate of the patient, while a prominent frequency of 1.86 Hz may be identified in the analysis but not immediately related to a specific medical parameter. Identification of the medical significance of detected may be achieved indirectly by relation to monitored medical parameters (e.g., heart rate) and/or directly by further analysis 131. In the illustrated non-limiting example, image analysis and/or enhancement 133 may be applied at the detected frequencies, e.g., by applying 134 a temporal band pass filter at the detected frequencies to incoming US images 90 and/or enhanced (e.g., motion-compensated) ultrasound images 185. In the provided example, the prominent (temporal) frequency of 1.86 Hz that can be suspected as relating to the heart rate is indeed seen to correlate spatially to a blood vessel in the US images, and may be used to further enhance ultrasound images 185 to show the blood vessels more clearly. As discussed herein (see, e.g., tissue cooling model 116), the cooling effects and bubble transport effects of the blood vessel may be used in estimating damaged tissue regions 180.

In certain embodiments, identified bubbles 160 (see below) may be further identified as moving through blood vessels according to their movement pulsing frequency, possibly in correlation to previously identified blood vessels (e.g., using CT data). Detected medical parameters 135 may further be used to re-acquire the treatment region in case of patient movements. First, patient movements themselves may be monitored and used to indicate return of the patient to an original posture, and second, the regularity of medical parameters 135, e.g., in terms of frequency, may be used to identify the focal plane prior to the patient movement and re-establish key frames that correspond to the treatment region. Reacquisition of the treatment regions, or tracking failure recovery, may be achieved by any of the registration methods disclosed herein, possibly utilizing the data gathered until the loss of tracking, e.g., concerning image characteristics of the tracked region, and/or utilizing images in orthogonal planes as disclosed herein.

In certain embodiments, ultrasound registration module 101 may be configured to detect out-of-plane frames 111 by decreases in the monitored correlation value(s) 110, which are larger than a specified threshold. For example, the frequency analysis may be used to detect regular returns of the treatment region to the plane of US measurements, and thereby to determine key frames 120 (see, e.g., FIG. 3). Moreover, the frequency analysis may be used to remove noise (e.g., speckle) from the images and thereby improve image quality.

It is noted that using correlation value(s) 110 provides a non-limiting example for processing sequential ultrasound images 90. Correlation among ultrasound images 90 may be carried out by a range of methods, including any of: sum of absolute differences (SAD), sum of squared differences (SSD), normalized cross correlation (NCC), kernel-based tracking algorithms, non-linear image registration using normalized gradient fields, 2D motion tracking using dense optical flow, Bayesian algorithms, motion estimation frameworks, etc.—as taught, e.g., in the Proceedings of the MICCAI 2014 workshop—Challenge on Liver Ultrasound Tracking, CLUST 2014—incorporated herein by reference in its entirety.

In certain embodiments, ultrasound registration module 101 may be configured to assess an image quality 105 of sequential ultrasound images 90 and remove low quality images. In certain embodiments, ultrasound registration module 101 may be configured to carry out image quality assessment 105 by machine learning 114 with respect to an automatically tagged databank 112 that is formed by ultrasound registration module 101 on formerly received ultrasound images 90. Tagging may be performed in various ways, e.g., in relation to various measures of image quality, in relation to measures of its usefulness in the registration process (e.g., similarity to specific key frames 120), etc. image quality 105 may be assessed by a range of methods, including artificial intelligence methods such as deep convolutional neural networks for no-reference and full-reference image quality assessments, that may relate to quantitative as well as qualitative aspects of the images and image parts relating to the ablation procedure.

In certain embodiments, sequential ultrasound images 90 may be captured in two mutually orthogonal planes or in 3D, and ultrasound registration module 101 may be configured to perform respective registration of sequential ultrasound images 90. Data from one orthogonal plane may be used to enhance registration in another plane. In certain embodiments, using two mutually orthogonal US planes (denoted x and y planes, may have a 90° angle between them, or have other angles making the x, y plane not perpendicular to each other) may be utilized in determining key frames 120 and if needed, re-acquiring the treatment region following patient movements, as out-of-plane movement with respect to one plane (e.g., x plane) may be followed and monitored at the other plane (e.g., y plane), and be used to identify the new out-of-plane images, after the movement has taken place—as movements are manifested in both planes. Ultrasound registration module 101 may be configured to monitor and control the intersecting line between the two planes and use it for registration of the ultrasound images in either of the planes. In certain embodiments, two planes may be used to derive an at least partly 3D US image, or an enhanced 2D US image, having details concerning the volumetric extent of the treated tissue, of the ablation region and of other features in the vicinity (e.g., blood vessels). In certain embodiments, data from both planes may be used to verify that the ablation region covers the full required volume, and that the ablation procedure avoids damage around the lesion (see safety module 103 below).

Ultrasound image-guided system 100 may further comprise ablation monitoring module 102 configured to identify a start of ablation 150 by detecting a change in correlation value(s) 110, monitored by ultrasound registration module 101, which occurs within a specified duration and is above a specified threshold. Start of ablation 150 may be monitored during the ablation procedure to identify new ablation starts, e.g., when multiple power sources are used (e.g., multiple RF electrodes or laser focal points) or when power sources are used intermittently. In case of separate ablation loci, ablation monitoring module 102 may be configured to integrate the damaged tissue regions from the separate ablation loci.

FIG. 4 provides schematic non-limiting examples for detecting start of ablation 150, according to some embodiments of the invention. Detection of changes in incoming images 90, that are defined by specific parameters, are illustrated as probabilities in images 151, derived from changes in images 90, e.g., using frequency analysis 131. Ablation monitoring module 102 is configured to detect start of ablation 150, possibly in relation to the detected tip of ablation tool 80, without requiring data from tool 80 itself. As illustrated in FIG. 4, multiple (simultaneous and/or consecutive) events of start of ablation 150 may be detected independently, and overcome prior art difficulties such as masking by needle tip reflection and disturbances of noise and motion. Furthermore, detection of start of ablation 150 provides the exact timing of damage formation and enhances segmentation accuracy.

Ablation monitoring module 102 may be further configured to identify bubbles 160 formed by ablation in the registered ultrasound images and/or to detect bubble movements 170 in the registered ultrasound images. It is emphasized that disclosed systems provide detection of bubble movement 170 on grayscale, B-mode ultrasound images (e.g., not requiring Doppler processing that reduces the spatial and temporal resolution), at least according to key frames 120 and/or periodic change(s) 130 identified by ultrasound registration module 101. The dynamics of bubble movements 170 may be used to distinguish tissue regions that still have blood supply to them (by the blood vessels that evacuate the bubbles) from tissue regions that have no viable blood supply to them (in which bubbles are static and are not evacuated)—the latter corresponding to tissue that would consequently atrophy and can be included in demarcated tissue 180, even is not directly and sufficiently damaged by the ablation procedure. In this way, bubble monitoring can be used to predict resulting indirect tissue damage, which in the prior art can be detected only by waiting 24 hours and performing another imaging procedure (see the validation of this predictive ability in the experimental results below).

In certain embodiments, ablation monitoring module 102 may be configured to identify stopping bubble movements 170, which may be used to indicate collapsed blood vessels. Collapsed blood vessels (and tissue supplied thereby) may be then added to demarcated damaged tissue 180.

FIG. 5 provides schematic non-limiting examples for monitoring the dynamics of bubble movements 170, and its relation to blood vessels, according to some embodiments of the invention. Enhanced ultrasound image 185A illustrates damaged tissue 180 in contact with intact blood vessels 172 supporting bubble movements 171 and providing cooling effects 116 that may be modelled. In forming enhanced ultrasound image 185B, ablation monitoring module 102 may be configured to color-code damaged tissue 180, intact blood vessels 172 and damaged blood vessels 174, which may be identified by the stopping of bubble movements 170. According to the analysis, damaged tissue demarcation 180 may be applied, e.g., as in enhanced ultrasound image 185C, and be shown to develop with time into consecutive enhanced ultrasound images (e.g., 185D) as ablation increases the extent of the damage regions and as blood vessels are damaged, coagulated and collapse.

Ablation monitoring module 102 may be further configured to demarcate thermally damaged tissue region 180— dynamically and in real-time with respect to incoming sequential ultrasound images, and with respect to, and excluding, detected bubble movements 170. Specifically, the inventors have found out that bubble movement 170 may be used to indicate tissue that is not yet damaged, and therefore excluded from damaged tissue demarcation 180. Bubble movement 170 may be monitored with respect to specified frequencies, identified as relating to blood pulsation through the blood vessel (see heart rate identification above). Accordingly, the bubbles may be used as a contrast agent under US inspection to mark maintained and stopped blood flow in the ablation region. Stop of blood flow may be then used to indicate tissue damage and to demarcate additions to the damaged regions, as disclosed herein.

Ablation monitoring module 102 may be further configured (see, e.g., FIG. 1C) to demarcate, dynamically and in real-time with respect to incoming sequential ultrasound images, intact blood vessels 172 with respect to the detected bubble movements 170. In certain embodiments, ablation monitoring module 102 may be configured to correlate demarcated blood vessels 172 with blood vessels identified in an enhanced preparatory CT image 175. The correlation may be used as a verification tool, as a way to enhance the CT images and/or for ablation analysis 104 and/or simulation and planning 106 of consecutive ablation. Ablation monitoring module 102 may be further configured to identify damaged blood vessels 174, dynamically and in real-time with respect to incoming sequential ultrasound images, e.g., according to detected stops of bubble movements 170. Ablation monitoring module 102 may be further configured to add identified damaged blood vessels 174 to demarcated thermally damaged tissue region 180. For example, the inventors have identified a typical signature for blood vessel collapses 176 that can be used to identify such events and update demarcated damaged region 180 accordingly, by adding the area of collapsed blood vessel 176 thereto.

In certain embodiments, ablation monitoring module 102 may be further configured to characterize thermally ablated tissue by its biological signature, namely by the typical ways the tissue reacts to the thermal ablation—e.g., the types of bubbles formed and their propagation through the tissue, the speed at which the damage develops in the tissue, the distribution of blood vessels through the tissue etc. It is noted that the biological signature may also be used to enhance the ablation, e.g., tumors supplied by a large number of blood vessels may be ablated slower than healthy tissue due to the extensive cooling of the ablation region provided by the blood vessels. Hence, the speed the ablation progressed may be used to characterize the tissue that is being ablated and possibly used to fine-tune the ablation procedure itself.

In certain embodiments, additional data, e.g., from other ultrasound modes, may be used to further enhanced disclosed B-mode-based US image processing. For example, M-mode or Doppler data may be derived and used to enhance flows in the presented US images.

FIG. 1D illustrates schematically an algorithm flow for estimating liver tissue damage, according to some embodiments of the invention. The algorithm flow may comprise preparation stage 202, perception stage 204 (possibly carried out at least partly by ablation monitoring module 102) and segmentation stage 206 (possibly carried out at least partly by ablation analysis module 104), which may also be part of method 200 described in FIG. 10 below. Disclosed algorithms may be configured receive ultrasound images in real-time and deliver enhanced ultrasound images 185 that comprise indications for the effects of ongoing thermal ablation, such as demarcated damaged tissue 180. Examples for such indication may comprise outlining of the damaged region, filing of the damaged region with one or more colors, modification of the ultrasound image pixels (e.g., making pixels corresponding to damaged tissue darker or lighter in the display), adding color to the gray scale image etc. For example, any of these modifications may include incorporating data from a parametric coagulation map 181 described below (see FIG. 7A) into enhanced ultrasound images 185.

For example, preparation stage 202 may comprise ultrasound registration by ultrasound registration module 101 and image quality assessment 105. Perception stage 204 may comprise detection of the start of ablation 150, analysis of the fluid dynamic of bubble movements 171 (e.g., in relation to bubble development and surrounding blood vessels and indicative of their state as disclosed in FIG. 1C) and shadowing detection 191, e.g., according to geometrical considerations relating to the bubble development with respect to the position and orientation of the ultrasound transducer. Segmentation stage 206 may comprise ablation segmentation 182, e.g., including identification and categorization of tissue damage in segments (one or more pixels) of the images, ablation segmentation in shadowed regions 184, e.g., further including enhancement 192, organ segmentation 186, e.g., relating the tissue damage to anatomic details of the treated region of the respective organ, such as the liver, and optionally 3D damage rendering 188 which may be projected on the 2D ultrasound images in various manners and/or be represented in a 3D manner, either directly (e.g., using a 3D representation) or indirectly (e.g., allowing the user to change the plane of the 2D image).

In certain embodiments, ablation monitoring module 102 may be further configured to define a shadowed region 190 in sequential ultrasound images 90 with respect to the identified bubbles 160, and enhance 192 shadowed region 190 to determine a distal boundary of thermally damaged tissue region 180. The definition of shadowed region 190 may be carried out with respect to detected bubbles 160 and/or with respect to detected bubble movements 170. In demarcated damaged tissue 180, shadowed regions 190 may be enhanced to enable better distinguishing of tissue damage and of intact and damaged blood vessels and blood vessel collapses 172, 174, 176, respective—and include these in demarcated damaged tissue 180.

It is noted that in addition to shadowed regions 190 due to bubbles, which is dynamic and may change during the ablation treatment, additional shadowing may also be present in images 90 due to bones (e.g., ribs) and other tissues and elements which are opaque to ultrasound. Such shadowing is more static in the sense that while it may change between images 90 due, e.g., to movements and periodic changes 130, it typically does not develop in time. As the former (dynamic shadowing related to the treatment) is closer to the treatment region and is transient and changing while the latter (static shadowing, usually unrelated to the treatment) is more stable and constant—the former pose a greater challenge which is discussed herein. Clearly, corresponding procedures may be applied to the latter as well.

Ultrasound registration module 101 and/or ablation monitoring module 102 may be configured to apply a temporal and a directional analysis on ultrasound images 90 to determine shadowed regions 190 and the regions in images 90 they influence and are influenced by. The directional analysis may be applied in radial and/or tangential directions.

FIG. 6 provides non-limiting examples for handling shadowed regions 190, according to some embodiments of the invention. Static shadowing 191, which is usually unrelated to the treatment but to ultrasound-opaque material in images 90, is usually cast over larger sections of images 185, and is typically on the sides of the images and apart from the treatment region, as therefore required relatively little image processing. However, alerts may be provided in case the extent of the ablated tissue approaches the shadowed regions, as shadows 191 are typically dark (e.g., bone shadow) and may limit the system's ability to monitor the ablation procedure. Straightforward image enhancement may be applied in shadowed regions 191, e.g., by increasing contrast (enhancing differences between pixels) and/or re-scaling the gray scale to cover the narrowed gray range within shadowed regions 191. Also, shadowed image regions 191 may be at least partly excluded from the registration process to enhance its efficiency, e.g., in case shadowed regions 191 may impede detection of periodic changes 130 (e.g., with respect to processing speed, memory requirements etc.).

Bubbles 160 created during ablation are highly reflective and therefore create shadows 192 which are typically dynamic with bubble movements, local in the region of treatment, and less dark and more diffuse than static shadowing 191. Dynamic shadowing 192 related to the treatment typically requires more detailed analysis as it may strongly influence the disclosed estimation of tissue damage. As the ablated region expands, the size and influence of bubble shadowing 192 on the derivation of damaged regions 180 become more significant and dedicated processing of shadowed region 192 may be applied as disclosed above (e.g., enhancement of contrast and/or brightness, separate analysis by ablation monitoring module 102 etc.). As illustrated schematically in FIG. 6, the spatial extent of shadowed regions 192 may be calculated with respect to all identified bubbles and bubble-containing regions 161 detected by ablation monitoring module 102, with respect to the direction of the ultrasound source (e.g., in the corresponding radial direction, or in an approximated direction depending on the type of the source). The results of the calculations may be expressed as masks that correspond to shadowed regions 192 and be spatially merged for multiple identified bubbles and bubble-containing regions 161. Image processing within calculated shadowed regions 192 may be carried out as disclosed above.

Additionally or complementarily, damage to tissue may be estimated with regard to the derivative of the grayscale in images 90, and to some extent at least overcome the hinderance posed by shadowing. Enhancement of image 185 may be applied according to the derivative of the grayscale to enhance damaged tissue demarcation 180. Additionally or complementarily, the detection threshold may be reduced in shadowed regions 190 and/or the grayscale may be normalized in shadowed regions 190. Machine learning, such as deep learning procedure, may be applied to detecting shadowing through the dynamic changes caused by ablation—to enhance analysis of the damaged tissue.

Tissue characterization and image segmentation may be further enhanced with respect to effects the thermal ablation has on the respective tissues. Ablation analysis module 104 may be configured to distinguish live from dead tissue (including predicting tissue parts that would atrophy following destruction of corresponding blood vessels), to distinguish among types of tissues (e.g., with relation to the amount, sizes and forming conditions of bubbles in them) and possibly incorporate models for heat dissipation and sound speed through different tissue types. Labels may be added to enhanced ultrasound image 185 to indicate the segmentation and/or the identified tissue types.

FIG. 7A is a high-level schematic illustration of a relation between bubble release and tissue coagulation, according to some embodiments of the invention. Bubble identification 160 and damaged tissue demarcation 180 may be carried out with respect to the following analysis of the spatiotemporal behavior of local thermal bubble activity induced by the thermal treatment. As shown schematically in FIG. 7A, typical bubble behavior during thermal ablation can be divided into three main phases. During the initial phase (denoted Phase 1), bubbles (comprising e.g., nitrogen and/or oxygen gases) are being released from cells and from connective tissue due to the thermal treatment, and, at the same time, are being partially removed from the region by the local blood circulation. Accordingly, the bubble concentration in the respective region increases at a rate that represents the balance between the processes of bubble release and evacuation. During the consecutive phase (denoted Phase 2), the blood vessels coagulate and stop evacuating the bubbles that are being formed. Accordingly, the bubbles concentration rate increases as the bubbles continue to form but are not evacuated. Finally, during the final phase (denoted Phase 3), the bubble concentration reaches saturation due to complete tissue coagulation. It is noted that tissues that are not coagulated but in which blood supply has been cut-off undergo apoptosis due to ischemia, typically within a day or too and can hence also be considered damaged tissue.

Quantitative estimation of damaged tissue 180 may be carried out by measuring the bubble concentration throughout the tissue according to the denoted phases. For example, in some embodiments, bubble concentration may be estimated using the tissue echogenicity (also termed integrated back scatter—IBS), e.g., as being proportional thereto.

It is emphasized that bubble concentration may be estimated using regular, two dimensional B mode ultrasound images, at maximal temporal and spatial resolution provided by the respective ultrasound device, and allow corresponding high resolution ablation ultrasound-based guidance as described herein. For example, FIG. 7A further provide an example for parametric coagulation map 181 derived in relation to the temporal gradient of the B mode ultrasound image at each point, formally expressed by Equation 1, with $\sigma(t)$ denoting the parametric coagulation map, B(t) denoting the B-mode image values, which are proportional to IBS(t) denoting the local tissue echogenicity as function of time.

$$\sigma(t) = (\partial B(t))/\partial t \text{ (with } B(t) \propto \log IBS(t))$$  Equation 1

It is noted that under this definition, the parametric coagulation map is not sensitive to the incident ultrasonic intensity and therefore is also not affected by bubble absorption artefacts (e.g., due to bubbles formed between the point of interest and the ultrasound transducer, and see discussion of shadowing above).

FIG. 7B is a high-level schematic illustration of a color representation of bubble development phases, according to some embodiments of the invention. Derived parametric coagulation map 181 may be displayed in various manners, e.g., as a color overlay map on the ultrasound image, with each pixel represented either by the grayscale value B or by a color indicating the local state of ablation (e.g., using three colors for phases 1, 2 and 3 described above). A non-limiting example for such display is provided in FIG. 7B, in which a continuous color scale is used to indicate tissue damage due to radiofrequency ablation treatment after 40 sec of pre-treatment (a), after 20 sec of treatment (b), after 25 sec of treatment (c), after 30 sec of treatment (d), after 35 sec of treatment (e) and after 40 sec of treatment (f).

It is noted that parametric coagulation map 181 does not depend on knowledge of tissue or patient-specific parameters to determine the ablation zone morphology. Since $\sigma(t)$ directly estimates and is used to image both tissue necrosis and the prospective (e.g., after 24 hours) tissue apoptosis in real-time, the physician gets a real-time feedback on the destruction profile and can adjust the ablation process to ensure the complete destruction of tumor 70 and the desired margin, with only minimal damage to the surrounding tissue. It is emphasized that all information required to provide the physician the required information (parametric coagulation map 181) is derived from commonly available B-mode ultrasound images.

FIG. 7C is a high-level schematic illustration of sequential ultrasound images 90, enhanced (185) with respective demarcated damaged tissue regions 180, according to some embodiments of the invention. As illustrated in FIG. 7C, starting from initial ablation 81, demarcated damaged tissue regions 180 grows gradually as the thermal ablation proceeds, until reaching its final size and form denoted as coagulation map 181. It is noted that enhanced ultrasound images 185 may comprise one or more indications for the effects of ongoing thermal ablation, e.g., outlining of the damaged region, filing of the damaged region with one or more colors, modification of the ultrasound image pixels (e.g., with regard to their brightness), addition of color to the gray scale image, e.g., corresponding to parametric coagulation map 181, etc. The accumulation of demarcated area from image to image reflects the detected bubbles, ceasing bubble movements and blood vessel collapses that occur during the thermal ablation procedure.

FIGS. 7D and 7E are high-level schematic examples for gray level histograms 152, according to some embodiments of the invention. In certain embodiments, ablation monitoring module 102 may be further configured to derive gray level histograms 152 of specified regions and analyses histograms 152 to identify start of ablation 150, bubbles 160 and bubble movements 170, as well as image artefacts. For example, typical histogram signatures may be identified, which correspond to any of start of ablation 150, bubbles 160 and bubble movements 170, as well as to tissue types, and ablation monitoring module 102 may be configured to detect and identify these histogram signatures. In certain embodiments, machine learning procedures (e.g., deep learning) may be employed to characterize the histogram signatures for the different cases and/or for tissue characterization. In certain embodiments, the histograms may be further processed, for example, by modifying them to lines that indicate the relative frequencies of the different grayscale levels in histograms 152 histograms 152, as illustrated schematically, for specific times, in FIG. 7D, and corresponding to individual curves in FIG. 7E. The lines may be used for further analysis or for display, with histogram signatures expressed in typical lines that may be related to the respective event (e.g., start of ablation 150, bubbles 160 and bubble movements 170).

Ultrasound image-guided system 100 may further comprise safety module 103 (see FIG. 1B) configured to detect, in real-time with respect to incoming sequential ultrasound images, safety boundaries 160 for the ablation procedure, track safety boundaries 160 with respect to periodic changes 130 in sequential ultrasound images 90 (identified by ultrasound registration module 101), and alert 144 in case the ablation (as monitored by ablation monitoring module 102) approaches tracked safety boundaries 142. For example, safety boundaries 160 may be defined as the boundaries of the treated organ (e.g., liver or liver lobes), adjacent critical structures (e.g., large arteries) or other types of tissue to which damage is to be avoided. Safety module 103 may this be configured to spare vital structures that are proximal to the site of treatment. It is noted that disclosed safety module 103 is configured to track 142 safety boundaries 160 through their continuous movements in ultrasound images 90, that result from natural movements (e.g., breathing and heart beating as examples of periodic changes 130) or movements of the ultrasound transducer.

FIGS. 8A and 8B provide non-limiting examples for tracking the treated region in enhanced ultrasound images 185, demonstrating the maintaining of registration 140 and tracking 142 through movements in images 185, according to some embodiments of the invention. In the figures, the treated region is circled, and is shown schematically to move back and forth, without loss of registration, in swings that correspond to the patient's breathing rate (FIG. 8A). FIG. 8B demonstrate schematically temporary loss of tracking and registration due to a strong movement of the patient, and quick regaining of registration and tracking. The figures demonstrate the stability and robustness of the disclosed registration and tracking procedures.

Simulation and planning module 106 may be configured to convert preparatory imaging data from, e.g., CT or MRI 86, such as 3D data, into data relevant to ultrasound, e.g., to provide demarcation of the tissue that is to be ablated (see the comparison of the damaged tissue to the tumor in the example below).

Simulation and planning module 106 may be configured to suggest operational parameters (e.g., intensity, duration, number and timing of ablation locations etc.) and/or spatial configuration (e.g., position and orientation) for ablation tool 80—to plan and/or simulate an upcoming ablation procedure. Simulation and planning module 106 may utilize preparatory imaging, e.g., 3D CT or MRI images (e.g., from CT system 86, see FIGS. 1C, 8A and 8B, and also the experimental data below). Simulation and planning module 106 may utilize ultrasound data gathered from previous or experimental procedures, relating types of thermal ablation with resulting tissue damage, with respect to tissue structures.

The data gathered during the thermal ablation procedure may be used to provide analysis thereof, e.g., via ablation analysis module 104. The data may further be accumulated and processed to provide simulation and planning of ablation procedures, e.g., via simulation and planning module 106.

In certain embodiments, simulation and planning module 106 may comprise a tissue cooling model 116, derived from various sources, such as any of ablation analysis module 104 and former procedures, preparatory CT or MRI images 86, heat and flow models etc. Tissue cooling model 116 may relate tissue structure, such as number and spatial configuration of blood vessels in the vicinity of the tissue that is to be treated, to the dispersal of heat applied by ablation tool 80 with specific operational parameters and at a specified spatial configuration.

In certain embodiments, analysis of preparatory CT images may provide the spatial configuration of blood vessels that surround the tissue that is to be ablated, including diagonal blood vessels which are not imaged in a single ultrasound (or CT) plane but contribute to tissue cooling and therefore to the extent and shape of the damaged tissue region. Diagonal blood vessels may be enhanced and used to plan the ablation procedure.

In certain embodiments, automated learning procedures may be implemented to enhance tissue cooling model 116 and/or to enhance analysis of preparatory imaging. For example, simulation and planning module 106 may be configured to predict the spatial configuration of blood vessels, to assess cooling effects of blood vessels and to provide estimations of predicted bubble movements once the ablation treatment has started.

Accordingly, given an upcoming procedure, simulation and planning module 106 may be configured to utilize tissue cooling model 116 to predict tissue damage under specific conditions and optimize the ablation procedure. Ablation monitoring module 102 may be further configured to monitor the ablation procedure with respect to the predictions from tissue cooling model 116 (e.g., concerning cooling effects and predicted bubble movements)—both to adjust ablation parameters during the procedure and to update tissue cooling model 116 if needed.

FIG. 1E is a high-level block diagram of exemplary computing device 109, which may be used with embodiments of the present invention. Computing device 109 may include a controller or processor 63 that may be or include, for example, one or more central processing unit processor(s) (CPU), one or more Graphics Processing Unit(s) (GPU or general purpose GPU—GPGPU), a chip or any suitable computing or computational device, an operating system 61, a memory 62, a storage 65, input devices 66 and output devices 67. Ultrasound image-guided system 100 and/or any of its modules such as ultrasound registration module 101, ablation monitoring module 102, safety module 103, ablation analysis module 104, image quality assessment module 105 and/or planning module 106—may comprise at least parts of the computer system as shown for example in FIG. 1E.

Operating system 61 may be or may include any code segment designed and/or configured to perform tasks involving coordination, scheduling, arbitration, supervising, controlling or otherwise managing operation of computing device 109, for example, scheduling execution of programs. Memory 62 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 62 may be or may include a plurality of, possibly different memory units. Memory 62 may store for example, instructions to carry out a method (e.g., code 64), and/or data such as user responses, interruptions, etc.

Executable code 64 may be any executable code, e.g., an application, a program, a process, task or script. Executable code 64 may be executed by controller 63 possibly under control of operating system 61. For example, executable code 64 may when executed cause the production or compilation of computer code, or application execution such as VR execution or inference, according to embodiments of the present invention. Executable code 64 may be code produced by methods described herein. For the various modules and functions described herein, one or more computing devices 109 or components of computing device 109 may be used. Devices that include components similar or different to those included in computing device 109 may be used, and may be connected to a network and used as a system. One or more processor(s) 63 may be configured to carry out embodiments of the present invention by for example executing software or code.

Storage 65 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, VR model data, parameters, etc, may be stored in a storage 65 and may be loaded from storage 65 into a memory 62 where it may be processed by controller 63. In some embodiments, some of the components shown in FIG. 1E may be omitted.

Input devices 66 may be or may include for example a mouse, a keyboard, a touch screen or pad or any suitable input device. It will be recognized that any suitable number of input devices may be operatively connected to computing device 109 as shown by block 66. Output devices 67 may include one or more displays, speakers and/or any other suitable output devices. It will be recognized that any suitable number of output devices may be operatively connected to computing device 109 as shown by block 67. Any applicable input/output (I/O) devices may be connected to computing device 109, for example, a wired or wireless network interface card (NIC), a modem, printer or facsimile machine, a universal serial bus (USB) device or external hard drive may be included in input devices 66 and/or output devices 67.

Embodiments of the invention may include one or more article(s) (e.g., memory 62 or storage 65) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

FIG. 9A is a high-level schematic illustration of an ultrasound display 195, according to some embodiments of the invention. Ultrasound display 195 may be associated, within ultrasound image-guided system 100, with thermal ablation unit 80 and ultrasound system 85, and comprise a repeatedly-updated B-mode ultrasound image 185, and at least one indication 197 of thermally damaged tissue, registered upon repeatedly-updated B-mode ultrasound image 185. Non-limiting examples for indication(s) 197, which may be combined and/or alternated, comprise a border 197A of the thermally damaged tissue and/or a colored area 197B indicating the thermally damaged tissue (see, e.g., FIG. 9A), which may be repeatedly updated as a corresponding thermal ablation procedure proceeds. Alternatively or complementarily, indication(s) 197 may comprise indications 197C of bubble formation (phase 1), bubble development in which both bubble formation and bubble evacuation by blood vessels occur (phase 2) and bubble saturation (phase 3) (see, e.g., FIGS. 7A and 7B above), which may be repeatedly updated as a corresponding thermal ablation procedure proceeds. In certain embodiments, ultrasound image 185 may be displayed in grayscale and indication 197, such as indications 197C of phases 1, 2 and 3 may be displayed in different colors, with phases 1, 2 and 3 defined per pixel according to a respective accumulation rate of monitored bubbles in sequential ultrasound images. Clearly, the colors may reflect a continuous parameter that corresponds, e.g., to the bubble accumulation rate, to the bubble motility or any other parameter used to quantify the degree of tissue damage for the respective pixel, and/or may be modified and/or made discrete to reflect any defined damage threshold.

In certain embodiments, ultrasound display 195 may be further configured to indicate safety boundaries for a corresponding thermal ablation procedure, e.g., according to safety module 103. In certain embodiments, ultrasound display 195 may be further configured to indicate medical parameters 135 derived from periodic changes 130 in sequential ultrasound images 90, such as the breathing rate and/or a heartbeat rate of the patient, e.g., according to ultrasound registration module 101. In certain embodiments, ultrasound display 195 may be configured to display repeatedly-updated B-mode ultrasound image 185 and indication(s) 197 of thermally damaged tissue in two mutually orthogonal planes.

Ultrasound image-guided system 100 may further be associated with a CT system 86 that is used to derive preparatory images of the tissue that is to be treated. Ultrasound display 195 may be further configured to relate displayed indication(s) 197 to CT-based image(s) of the tissue. FIG. 9B is a high-level schematic illustration of CT-based image(s) used for planning the ablation procedure, according to some embodiments of the invention. 3D anatomical models are illustrated for a liver tumor ablation procedure, indicating the positioning of ablation tool 80 and simulated ablation volume 82. In certain embodiments, at least part of the planning may be carried out by simulation and planning module 106 on US images, e.g., with respect to tissue cooling model 116 (see FIGS. 1A and 1C). At least part of the planning may be carried out and/or displayed using ultrasound display 195, which may be associated with simulation and planning module 106.

FIG. 10 is a high-level flowchart illustrating a method 200, according to some embodiments of the invention. The method stages may be carried out with respect to ultrasound image-guided system 100 and/or any of its modules described above, which may optionally be configured to implement method 200. Method 200 may be at least partially implemented by at least one computer processor, e.g., in an ultrasound system or in related systems. Certain embodiments comprise computer program products comprising a computer readable storage medium (see, e.g., FIG. 1E) having computer readable program embodied therewith and configured to carry out the relevant stages of method 200. Method 200 may comprise the following stages, irrespective of their order.

Method 200 comprises performing ultrasound image registration in real-time (or close to real-time) (stage 201), with respect to a plurality of sequential ultrasound images (e.g., incoming images), by calculating and monitoring at least one correlation value between the sequential ultrasound images (stage 220), identifying a plurality of key frames from values of the calculated at least one correlation value (stage 222), identifying at least one periodic change in the sequential ultrasound images, from values of the calculated at least one correlation value (stage 224), and performing the ultrasound image registration by correlating pixels in sequential key frames that have a same phase with respect to the identifying at least one periodic change (stage 230). Method 200 may comprise Using ultrasound images in two mutually orthogonal planes or in 3D (stage 205).

It is noted that the correlation value(s) or equivalent measures may be calculated by a range of methods, such as sum of absolute differences (SAD), sum of squared differences (SSD), normalized cross correlation (NCC), kernel-based tracking algorithms, non-linear image registration using normalized gradient fields, 2D motion tracking using dense optical flow. Bayesian algorithms, motion estimation frameworks, etc.

In certain embodiments, method 200 may comprise deriving medical parameters such as a breathing rate and/or a heartbeat rate, from the identified periodic change(s) (stage 210). Method 200 may further comprise detecting out-of-plane frames by detecting decreases in the monitored correlation value(s), which are larger than a specified threshold (stage 212). Method 200 may comprise assessing an image quality of the sequential ultrasound images and removing low quality images (stage 214). In certain embodiments, assessing 214 may be carried out by automatically tagging the images, e.g., in relation to formerly received images, possibly forming an automatically tagged databank, and using machine learning to assess the image quality of incoming images with respect to the tagged images.

Method 200 further comprises monitoring thermal ablation using B-mode ultrasound images (stage 240), by identifying a start of ablation by a change in the monitored correlation value(s) that occurs within a specified duration and is above a specified threshold (stage 250), identifying bubbles formed by ablation in the registered ultrasound images (stage 260) and/or detecting bubble movements in the registered ultrasound images (stage 270), e.g., in B mode ultrasound images, at least according to the identified key frames and/or the identified periodic change(s).

Method 200 may further comprise demarcating, dynamically and in real-time with respect to incoming sequential ultrasound images, a thermally damaged tissue region with respect to, and excluding, the detected bubble movements (stage 280). Method 200 may comprise demarcating, dynamically and in real-time with respect to incoming sequential ultrasound images, intact blood vessels with respect to the detected bubble movements (stage 282). In certain embodiments, method 200 may comprise correlating the demarcated blood vessels with blood vessels identified in an enhanced preparatory CT image (stage 285). Method 200 may further comprise identifying, dynamically and in real-time with respect to incoming sequential ultrasound images, damaged blood vessels according to detected stops of bubble movements (stage 290) and possibly adding the identified damaged blood vessels to a demarcated thermally damaged tissue region (stage 292).

In certain embodiments, method 200 may further comprise defining a shadowed region in the sequential ultrasound images with respect to the identified bubbles (stage 300), and enhancing the shadowed region to determine and/or demarcate a distal boundary of a thermally damaged tissue region (stage 305).

In certain embodiments, method 200 may further comprise detecting, in real-time with respect to incoming sequential ultrasound images, safety boundaries for an ablation procedure (stage 310), tracking the safety boundaries with respect to the identified periodic change(s) in the sequential ultrasound images (stage 312), and alerting in case the ablation approaches the tracked safety boundaries (stage 315).

Disclosed systems and methods were validated in an experimental setting, comparing demarcated damaged tissue 180 to contrast enhance CT (CECT) images taken 24 hours after the thermal RF ablation of 20 liver tumors in 19 patients. Parametric coagulation map 181 were derived according to Equation 1 from ultrasound images 90 that were obtained during 80 second treatments at 33 msec inter-frame periods. Parametric coagulation map 181 were then used to derive demarcated damaged tissue 180.

FIGS. 11A-11C provide respective illustrations of the compared damaged tissue area, a Bland-Altman plot presenting the level of similarity between demarcated damaged tissue 180, and a comparative experimental image, according to some embodiments of the invention and damaged tissue as measured by CECT 24 h post ablation, as measured in the prior art. The comparison was carried out using three metrics defined in Equations 2, with respect to the areas denoted in FIG. 11A as true positive (TP) for overlaps of demarcated damaged tissue 180 and damaged tissue measured by CECT 75, false positive (FP) for demarcated damaged tissue 180 extending beyond damaged tissue measured by CECT 75 and false negative (FN) for damaged tissue measured by CECT 75 extending beyond demarcated damaged tissue 180. True negative (TN) denotes tissue area outside both demarcated damaged tissue 180 and damaged tissue measured by CECT 75.

Sorensen–Dice coefficient=$2TP/(FN+2TP+FP)$

Sensitivity metric=$TP/(TP+FN)$

Precision metric=$TP/(TP+FP)$         Equations 2

FIG. 11B illustrates, using a Bland-Altman plot (comparing the differences between the areas provided by the two measurement methods to their averages), that the average difference between the total lesion area assessed by demarcated damaged tissue 180 and the damaged tissue as measured by CECT 24 h post ablation was $\mu=0.02$ cm$^2$ with a standard deviation $\sigma=0.2$ cm=(95% of the measurements are within the indicated $\pm 2\sigma$), compared with the average lesion size, measured by both methods as $5.03\pm 0.2$ cm$^2$. Accordingly, disclosed methods and systems provide highly accurate results that correspond very well to prior art post-ablation measurements.

FIG. 11C presents a comparative experimental image, in which demarcated damaged tissue 180 (as the solid red area) is compared to the actual damaged tissue as imaged by 24 h post treatment CECT (blue area that overlaps the red area). It is noted that not only do the damaged regions match, but they do so in also in cases in which the damage deviates significantly from the theoretical elliptical shape (see schematic illustration in FIG. 1A for consecutively heated regions 82). Such shapes occur, e.g., in the vicinity of a relatively large blood vessel that is not damage during the thermal ablation and therefore keeps cooling the tissue surrounding it, as can vie seen in the dynamic representation of bubble movements 170.

Disclosed procedures, including CT data transfer to system 100, correlation and registration of 3D CT data with 2D US images 90, US registration 140, and the calculation, analysis and demarcation of damaged tissue 180—have been validated in test performed with Fraunhofer Institute for Digital Medicine MEVIS.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment". "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An ultrasound display interface generated by a computer program product comprising a non-transitory computer readable storage medium having computer readable program embodied therewith and configured to display ultrasound images, during a thermal ablation procedure, the computer readable program-configured to:
   repeatedly update received B-mode ultrasound images, derive therefrom correlation values among the ultrasound images, and display the repeatedly-updated B-mode ultrasound images on the display interface,
   derive and repeatedly update at least one indication of thermally damaged tissue,
   register the at least one indication of thermally damaged tissue upon the displayed repeatedly-updated B-mode ultrasound image, and
   display the repeatedly updated at least one indication of thermally damaged tissue on the display interface according to the registration,
   wherein the registration is carried out by identifying a plurality of key frames using the derived correlation values among the received sequential ultrasound images, identifying at least one periodic change in the sequential ultrasound images, from the derived correlation values among the received sequential ultrasound images, and performing the ultrasound image registration by correlating pixels in sequential key frames that have a same phase with respect to the identified at least one periodic change, and
   wherein the at least one indication of thermally damaged tissue is derived only from analysis of the repeatedly-updated B-mode ultrasound images, using the derived correlation values.

2. The ultrasound display interface of claim 1, wherein the at least one indication comprises a border of the thermally damaged tissue, which is repeatedly updated as a corresponding thermal ablation procedure proceeds.

3. The ultrasound display interface of claim 1, wherein the at least one indication comprises a colored area indicating the thermally damaged tissue, which is repeatedly updated as a corresponding thermal ablation procedure proceeds.

4. The ultrasound display interface of claim 1, wherein the at least one indication comprises indications of bubble formation (phase 1), bubble development in which both bubble formation and bubble evacuation by blood vessels occur (phase 2) and bubble saturation (phase 3), which are repeatedly updated as a corresponding thermal ablation procedure proceeds.

5. The ultrasound display interface of claim 4, wherein the ultrasound image is in grayscale and the indication of phases 1, 2 and 3 is in different colors.

6. The ultrasound display interface of claim 4, wherein the phases 1, 2 and 3 are defined per pixel according to a respective accumulation rate of monitored bubbles in sequential ultrasound images.

7. The ultrasound display interface of claim 1, further configured to indicate safety boundaries for a corresponding thermal ablation procedure.

8. The ultrasound display interface of claim 1, further configured to indicate medical parameters derived from periodic changes in sequential ultrasound images, the medical parameters comprise a breathing rate and/or a heartbeat rate.

9. The ultrasound display interface of claim 1, further configured to display the repeatedly-updated B-mode ultrasound image and the at least one indication of thermally damaged tissue in two mutually orthogonal planes.

10. The ultrasound display interface of claim 1, further configured to display the at least one indication upon a CT-based display of a tissue that is to be treated, wherein the display is carried out with respect to the registration of the thermally damaged tissue on the ultrasound image.

11. A computer program product comprising a non-transitory computer readable storage medium having computer readable program embodied therewith and configured to carry out ultrasound image registration with respect to a plurality of sequential ultrasound images, the computer readable program comprising:

computer readable program configured to derive correlation values among the sequential ultrasound images by correlating the received sequential ultrasound images, irrespective of any given external structure, computer readable program configured to identify, from the received images, a plurality of key frames using the derived correlation values among the received sequential ultrasound images, computer readable program configured to identify at least one periodic change in the sequential ultrasound images, from derived correlation values among the received sequential ultrasound images, and computer readable program configured to perform the ultrasound image registration by correlating pixels in sequential key frames that have a same phase with respect to the identified at least one periodic change.

12. An ultrasound registration module, configured to:

derive correlation values among received sequential ultrasound images by correlating the received sequential ultrasound images, irrespective of any given external structure, identify a plurality of key frames using the derived correlation values among the received sequential ultrasound images, identify at least one periodic change in the sequential ultrasound images, from the derived correlation values among the received sequential ultrasound image, and perform ultrasound image registration by correlating pixels in sequential key frames that have a same phase with respect to the identified at least one periodic change, wherein the ultrasound image registration is performed irrespective of any external model.

13. The ultrasound registration module of claim 12, further comprising an ultrasound imaging module configured to display the received sequential ultrasound images, wherein the ultrasound registration module is configured to process ultrasound images with respect to a type of the ultrasound imaging module.

14. The ultrasound registration module of claim 12, further configured to derive medical parameters, comprising a breathing rate and/or a heartbeat rate, from the identified at least one periodic change.

15. The ultrasound registration module of claim 12, further configured to detect specific received ultrasound images that are out-of-plane frames with respect to a majority of the received ultrasound images, by decreases in the correlation values, which are beyond a specified threshold.

16. An ultrasound image-guided system for thermal ablation, the system comprising:

the ultrasound registration module of claim 12, configured to receive a plurality of sequential ultrasound images, and an ablation monitoring module, configured to identify a start of ablation by a change in the correlation values, calculated by the ultrasound registration module, which occurs within a specified duration and is above a specified threshold.

17. The ultrasound image-guided system of claim 16, wherein the ablation monitoring module is further configured to identify bubbles formed by ablation in the registered ultrasound images and detect bubble movements in the registered ultrasound images.

18. The ultrasound image-guided system of claim 17, wherein the ablation monitoring module is further configured to detect the bubble movements on B mode ultrasound images, at least according to the key frames and/or the at least one periodic change identified by the ultrasound registration module, and to demarcate, dynamically and in real-time with respect to incoming sequential ultrasound images, a thermally damaged tissue region with respect to, and excluding, the detected bubble movements.

19. The ultrasound image-guided system of claim 16, wherein the ablation monitoring module is further configured to define a shadowed region in the sequential ultrasound images with respect to the identified bubbles, and enhance the shadowed region to determine a distal boundary of a thermally damaged tissue region and to define a shadowed region in the sequential ultrasound images with respect to the identified bubbles, and enhance the shadowed region to demarcate a distal boundary of the thermally damaged tissue region.

20. The ultrasound image-guided system of claim 16, further comprising a safety module, configured to:

detect, in real-time with respect to incoming sequential ultrasound images, safety boundaries for an ablation procedure, track the safety boundaries with respect to the at least one periodic change in the sequential ultrasound images identified by the ultrasound registration module, and alert in case the ablation, as monitored by the ablation monitoring module, approaches the tracked safety boundaries.

* * * * *